(12) United States Patent
Sakai et al.

(10) Patent No.: US 8,617,614 B2
(45) Date of Patent: Dec. 31, 2013

(54) SUSTAINED RELEASE PREPARATION FOR TISSUE REGENERATION THERAPY

(75) Inventors: Yoshiki Sakai, Mishima-gun (JP); Takahiro Uchida, Nishinomiya (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 479 days.

(21) Appl. No.: 12/446,157

(22) PCT Filed: Oct. 18, 2007

(86) PCT No.: PCT/JP2007/070340
§ 371 (c)(1),
(2), (4) Date: Apr. 17, 2009

(87) PCT Pub. No.: WO2008/047863
PCT Pub. Date: Apr. 24, 2008

(65) Prior Publication Data
US 2010/0323026 A1    Dec. 23, 2010

(30) Foreign Application Priority Data

Oct. 19, 2006  (JP) ................................. 2006-285357

(51) Int. Cl.
*A61K 9/50* (2006.01)
*A61K 31/44* (2006.01)
*A01N 43/40* (2006.01)

(52) U.S. Cl.
USPC ......................................... 424/501; 514/357

(58) Field of Classification Search
USPC ....................................................... 424/501
See application file for complete search history.

(56) References Cited

U.S. PATENT DOCUMENTS

| | | | |
|---|---|---|---|
| 5,942,241 A | 8/1999 | Chasin | |
| 5,993,855 A | 11/1999 | Yoshimoto | |
| 6,514,516 B1 | 2/2003 | Chasin | |
| 6,521,259 B1 | 2/2003 | Chasin | |
| 6,524,607 B1 | 2/2003 | Goldenheim | |
| 2003/0185873 A1 | 10/2003 | Chasin | |
| 2006/0069018 A1* | 3/2006 | Sakai et al. | ............ 514/12 |
| 2006/0233883 A1 | 10/2006 | Ishihara | |

FOREIGN PATENT DOCUMENTS

| | | |
|---|---|---|
| EP | 1563846 A1 | 8/2005 |
| JP | 6-87811 A | 3/1994 |
| JP | 9-077657 A | 3/1997 |
| JP | 10-502673 A | 3/1998 |
| JP | 2006-521367 A | 9/2006 |
| WO | 2004032965 A1 | 4/2004 |

OTHER PUBLICATIONS

European search Report issued on Sep. 22, 2010 in the corresponding European Patent Application No. 07830074.6.
Office Action dated Dec. 4, 2012 issued by the Japanese Patent Office in counterpart Japanese Application No. 2008-539863.
Office Action dispatched Jun. 18, 2013 issued by the Japanese Patent Office in counterpart Japanese Application No. 2008539863.

* cited by examiner

*Primary Examiner* — Gina C Justice
*Assistant Examiner* — Michael B Pallay
(74) *Attorney, Agent, or Firm* — Sughrue Mion, PLLC

(57) ABSTRACT

The present invention provides a microsphere with a slow-release period from about two weeks to about four weeks following administration, to enable a higher content of a drug to be included, to suppress an initial burst of the drug, and to maintain an optimal, effective blood concentration during the slow-release period. In a microsphere containing a drug and polylactic acid/glycolic acid (PLGA) copolymer, the amount of PLGA copolymer per part by weight of the drug is from about 3 to about 10 parts by weight; the average particle size of the microsphere is from about 20 to about 50 μm; and (3) the PLGA copolymer has a weight-average molecular weight from about 10,000 to about 50,000 and a PLGA compositional ratio from about 75/25 to about 50/50. The microsphere promotes the production of various endogenous repair factors useful against various tissue disorders.

7 Claims, 2 Drawing Sheets

SUSTAINED RELEASE PREPARATION FOR TISSUE REGENERATION THERAPY

TECHNICAL FIELD

The present invention relates to microspheres comprising ({5-[2-({[(1E)-phenyl(pyridin-3-yl)methylene]amino}oxy)ethyl]-7,8-dihydronaphthalen-1-yl}oxy)acetic acid and a lactic acid/glycolic acid copolymer.

BACKGROUND ART

The development of long-term slow-release injections capable of continuously releasing a drug has hitherto been investigated with the aim of minimizing the number of times a medication is administered and thus improving drug compliance. In particular, numerous studies have been conducted on methods of controlled release involving the use of drug microspheres (sometimes abbreviated below as "MS") that use a polymer having a poor solubility in water. A biodegradable polymer is employed as this polymer so that, following release of the drug, the base does not remain at the site of administration. In particular, use is made of polylactic acid polymers (sometimes abbreviated below as "PLA") or lactic acid/glycolic acid copolymers (sometimes abbreviated below as "PLGA"), which have an established record of use in, for example, surgical suture thread and bone-anchoring bolts. These polymers are employed in injections of the LH-RH derivative Leuplin (trade name), which are commercially sold as slow-release injections, and in the long-acting somatostatin derivative Sandostatin (trade name) LAR.

Drugs commonly encapsulated within microspheres include peptides, proteins and nucleic acids, such as physiologically active peptides, various types of hormones, growth factors, antibodies, genes and various cell growth/differentiation factors. In the manufacture of microspheres, in general it is known that when the drug to be encapsulated has a higher molecular weight, microspheres which have a low initial burst and the release of which is easily controlled can be more easily manufactured.

By contrast, for a number of reasons, including the large initial burst, the difficulty of controlled release and the low drug content (encapsulation ratio), great difficulty has been encountered in efforts to prepare microspheres containing low-molecular-weight drugs; carrying out the stable release of such drugs in vivo and controlling the rate of release has proven to be exceedingly difficult. As a result, while there are cases in which low-molecular-weight compounds have been encapsulated (see Patent Document 1), none are available commercially as pharmaceutical preparations.

Meanwhile, the compound, ({5-[2-({[(1E)-phenyl(pyridin-3-yl)methylene]amino}oxy)ethyl]-7,8-dihydronaphthalen-1-yl}oxy)acetic acid (abbreviated below as "the present drug") is a low-molecular-weight compound which has a chemically stable non-prostaglandin (PG) skeleton, a $PGI_2$ receptor (IP) agonist action and a thromboxane (TX) $A_2$ synthetase inhibition activity. The present drug, because it has a $PGI_2$ agonist action, is known to be used in the prevention and/or treatment of, for example, thrombosis, arteriosclerosis, ischemic heart disease, gastric ulcers and hypertension (Patent Document 2).

However, concerns when the present drug is administered orally include side effects such as upper abdominal pain and diarrhea. When administered intravenously, side effects such as a hypotensive action associated with vasodilation, flushing and headaches, etc. are a concern. In particular, when the present drug is employed for, of the above-mentioned diseases, cardiovascular diseases such as arteriosclerosis and ischemic heart disease, etc. from the standpoint of the side effects and the therapeutic system, to prevent exposure to a high concentration of the drug in the digestive tract and a sudden rise in the blood concentration of the drug, to minimize the burden on the patient and to maximize the drug effects, there exists a keen desire for preparations which are capable of continuously maintaining the drug concentration with the smallest possible number of administration, including dosage forms of a type that continuously maintain the concentration of the drug in the tissue at the site of disease or blood concentration maintenance-type dosage forms such as intravenous drip infusions.

The local administration of microspheres containing the present drug has been investigated as a method for resolving the above problems, including the appearance of side effects and a sudden rise in the blood concentration of the drug. For example, Patent Document 3 discloses a long-acting preparation containing the present drug and PLGA, and states that this preparation was effective when locally administered in a rat arteriosclerosis obliterans (ASO) model. However, because the microspheres described in Patent Document 3 had a low drug content, the dose in which the microspheres themselves are administered increases, giving rise to an acidy problem. In addition, the release period for the present drug is short and the rate of release is not constant, as a result of which these prior-art microspheres have not succeeded in maintaining the blood concentration optimal for emergence of the drug effects over a fixed period of time.

Patent Document 1: JP-9-263545 A
Patent Document 2: JP-6-87811 A
Patent Document 3: WO 2004/032965

DISCLOSURE OF THE INVENTION

Problems to be Solved by the Invention

The object of the invention is to provide safe, easy-to-use microspheres which continuously release the present drug over an extended period of time, can include a high content of the drug, release the drug at a fixed rate and, during the period of release, maintain the drug in a blood concentration range optimal for manifestation of the drug effects.

Means for Solving the Problems

The inventors have conducted investigations with the aim of resolving the above problems. As a result, they have found that, in microspheres comprising the present drug and PLGA (which microspheres are also referred to below as "the inventive microspheres"), a specific combination of characteristics such as the weight-average molecular weight of the PLGA, the lactic acid/glycolic acid ratio in the PLGA, the average particle size of the microspheres, the weight ratio of the present drug and the PLGA, or the like has the unanticipated effects of imparting the ability to continuously release the drug over an extended period of one week or more and enabling the drug to be included within the microspheres in a higher content, thus enabling the dose of microspheres to be set within an optimal range at which an acidity problem does not arise. In addition, the inventors have discovered that the microspheres of the present drug are able to suppress an initial burst (i.e., the percentage of the drug remaining in a release test can be maintained at or above a fixed value) and, during the period of release, are able to maintain the blood concentration of the drug in the range optimal for manifesting the drug effects.

Accordingly, the present invention relates to:

[1] A two to four-week long-acting microsphere, comprising ({5-[2-({[(1E)-phenyl(pyridin-3-yl)methylene]amino}oxy)ethyl]-7,8-dihydronaphthalen-1-yl}oxy)acetic acid as a drug and a lactic acid/glycolic acid copolymer, wherein
(i) an amount of lactic acid/glycolic acid copolymer per part by weight of the drug is from 3 to 10 parts by weight,
(ii) the microsphere has an average particle size of from 20 to 50 μm, and
(iii) the lactic acid/glycolic acid copolymer has a weight-average molecular weight of from 10,000 to 50,000 and a lactic acid/glycolic acid compositional ratio of from 75/25 to 50/50,
and satisfying at least one of conditions (1) to (3) below:
(1) a remaining ratio of the drug after one hour in a release test is at least 90%;
(2) a remaining ratio of the drug after one day in a release test is at least 82%; and
(3) for a period of four weeks following administration, the drug is released at a fixed rate and the drug is maintained at a blood concentration of at least 0.01 ng/mL;
[2] The microsphere according to [1] above, wherein the content of lactic acid/glycolic acid copolymer per part by weight of the drug is from 4 to 8 parts by weight;
[3] The microsphere according to [1] above, wherein the microsphere has an average particle size of from 25 to 35 μm;
[4] The microsphere according to [1] above, wherein the lactic acid/glycolic acid copolymer ratio is 50/50;
[5] The microsphere according to [1] above, wherein the blood concentration of the drug is from 0.01 ng/mL to 150 ng/mL;
[6] An agent for preventing and/or treating arteriosclerosis obliterans, stroke, pulmonary fibrosis, pulmonary hypertension, asthma, diabetes and complications thereof, angina, myocardial infarction, renal failure, osteoarthritis, rheumatoid arthritis or osteoporosis, the agent comprising the microsphere of [1] above;
[7] A two-week long-acting microsphere, comprising ({5-[2-({[(1E)-phenyl(pyridin-3-yl)methylene]amino}oxy)ethyl]-7,8-dihydronaphthalen-1-yl}oxy)acetic acid as a drug and a lactic acid/glycolic acid copolymer, wherein
(i) an amount of lactic acid/glycolic acid copolymer per part by weight of the drug is from 4 to 8 parts by weight,
(ii) the microspheres has an average particle size of from 25 to 35 μm, and
(iii) the lactic acid/glycolic acid copolymer has a weight-average molecular weight of from 10,000 to 30,000 and a lactic acid/glycolic acid compositional ratio of 50/50,
and satisfying conditions (1) and (2) below:
(1) a remaining ratio of the drug after one hour in a release test is at least 90%;
(2) for a period of two weeks following administration, the drug is released at a fixed rate and the drug is maintained at a blood concentration of from 0.01 ng/mL to 150 ng/mL; and
[8] A four-week long-acting microsphere, comprising ({5-[2-({[(1E)-phenyl(pyridin-3-yl)methylene]amino}oxy)ethyl]-7,8-dihydronaphthalen-1-yl}oxy)acetic acid as a drug and a lactic acid/glycolic acid copolymer, wherein
(i) an amount of lactic acid/glycolic acid copolymer per part by weight of the drug is from 4 to 8 parts by weight,
(ii) the microspheres has an average particle size of from 25 to 35 μm, and
(iii) the lactic acid/glycolic acid copolymer has a weight-average molecular weight of from 30,000 to 50,000 and a lactic acid/glycolic acid compositional ratio of 50/50,
and satisfying conditions (1) and (2) below:
(1) a remaining ratio of the drug after one day in a release test is at least 82%;
(2) for a period of four weeks following administration, the drug is released at a fixed rate and the drug is maintained at a blood concentration of from 0.01 ng/mL to 150 ng/mL.

The drug used in the present invention is ({5-[2-({[(1E)-phenyl(pyridin-3-yl)methylene]amino}oxy)ethyl]-7,8-dihydronaphthalen-1-yl}oxy)acetic acid (CAS Registry No. 176391-41-6) of formula (A).

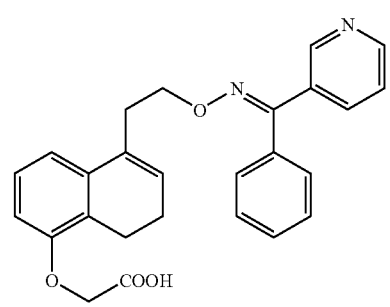

The present drug is cited in Example 2(g) of JP-6-87811 A, and can be prepared in accordance with a method described in the same publication. Alternatively, a salt of the present drug, such as a sodium salt or a hydrochloride salt, may be used in place of the present drug.

As used herein, the term "microspheres" refers to microspheres comprising the present drug and PLGA.

The PLGA used in the present invention is a biodegradable polymer. When microspheres made of PLGA are administered in vivo, first, water molecules rapidly penetrate the polymer and hydrate the PLGA, causing it to swell and causing hydrolysis to proceed throughout, as a result of which the molecular weight of the PLGA gradually decreases. Body fluids (moisture) infiltrate the microspheres within about 24 hours, leading to sufficient swelling. As the decline in the molecular weight of the PLGA proceeds, the domain structure breaks down and weakens, and the drug present therein diffuses out from between the weakened PLGA bonds and is released by dissolution. PLGA hydrolysis occurs both non-enzymatically and enzymatically, starting with the infiltration of body fluids (moisture), with the drug gradually being released as hydrolysis proceeds.

The PLGA used in the present invention may be produced by a well known method per se, or may be acquired as a commercial product. Illustrative examples of the PLGA used in the present invention include PLGA-7510 (produced by Wako Pure Chemical Industries, Ltd.; DL-lactic acid/glycolic acid=75/25; weight-average molecular weight, 10,000), PLGA-7515 (produced by Wako Pure Chemical Industries, Ltd.; DL-lactic acid/glycolic acid=75/25; weight-average molecular weight, 15,000), PLGA-7520 (produced by Wako Pure Chemical Industries, Ltd.; DL-lactic acid/glycolic acid=75/25; weight-average molecular weight, 20,000), PLGA-5010 (produced by Wako Pure Chemical Industries, Ltd.; DL-lactic acid/glycolic acid=50/50; weight-average molecular weight, 10,000), PLGA-5015 (produced by Wako Pure Chemical Industries, Ltd.; DL-lactic acid/glycolic acid=50/50; weight-average molecular weight, 15,000), PLGA-5020 (produced by Wako Pure Chemical Industries, Ltd.; DL-lactic acid/glycolic acid=50/50; weight-average molecular weight, 20,000), PLGA5-50 (also called PLGA5-1; produced by Mitsui Chemicals, Inc.; DL-lactic acid/glycolic acid=50/50; weight-average molecular weight, 50,000), PLGA75-50 (produced by Mitsui Chemicals, Inc.; DL-lactic acid/glycolic acid=75/25; weight-average molecular weight, 50,000), H1702-2 (produced by Mitsui Chemicals, Inc.; DL-lactic acid/glycolic acid=50/50; weight-average molecular weight, 18,000), H1702-3 (produced by Mitsui Chemicals, Inc.; DL-lactic acid/glycolic acid=50/50; weight-average molecular weight, 35,000), and H1702-4 (produced by Mitsui Chemicals, Inc.; DL-lactic acid/glycolic acid=50/50; weight-average molecular weight, 46,000) etc. Some of these PLGA's have a low molecular weight cutoff (weight-average molecular weight of from 1 to 3,000) or the like.

In the present specification, the weight-average molecular weight of PLGA refers to the polystyrene equivalent average molecular weight measured by gel permeation chromatography (GPC).

L-lactic acid, D-lactic acid or DL-lactic acid may be used as the lactic acid in the PLGA. DL-lactic acid is preferred.

When the microspheres of the invention are used to prevent and/or treat, of the subsequently mentioned indications, arteriosclerosis obliterans, stroke, pulmonary fibrosis, pulmonary hypertension, asthma, diabetes and complications thereof, angina, myocardial infarction, renal failure, osteoarthritis, rheumatoid arthritis or osteoporosis, the period of slow release is preferably from two to four weeks.

In the microspheres of the invention, the weight-average molecular weight of the PLGA may be selected as follows according to the targeted slow release period. For example, in the case of a two to four-week slow release period, an average molecular weight of from about 10,000 to about 50,000 is preferred. Of this range, when a two-week slow release period is targeted, the weight-average molecular weight of the PLGA is preferably from about 10,000 to about 30,000, more preferably from about 10,000 to about 20,000, and most preferably from about 20,000. When a four-week slow release period is targeted, the PLGA weight-average molecular weight is preferably from about 30,000 to about 50,000, more preferably from about 40,000 to about 50,000, and most preferably about 50,000.

The lactic acid/glycolic acid ratio in the PLGA may be selected as follows according to the targeted slow-release period. For example, when a two to four-week release period is targeted, the ratio is preferably from 75/25 to 25/75 (w/w), more preferably from 75/25 to 50/50 (w/w), and most preferably 50/50 (w/w).

In microspheres made using PLGA, the rate of release slows at a larger average particle size. However, in cases where the microspheres are administered subcutaneously, intramuscularly or locally within the diseased organ, at an average particle size of 10 μm or less, when the microspheres flow out into the vascular system, they may circulate throughout the body, stop at non-target sites such as the lungs, liver or kidneys, and release the drug at those sites, as a result of which the drug effects may fail to appear. On the other hand, at a particle size of 70 μm or more, passage through the syringe (which has a gauge of 25 G to 27 G) used during administration worsens, in addition to which, when such microspheres flow into the vascular system, they may obstruct capillaries, triggering an ischemic condition.

Therefore, the average particle size of the inventive microspheres may be suitably adjusted to avoid the above problems and in accordance with the targeted slow-release period. For example, in cases where the slow-release period is from two to four weeks, the average particle size is preferably from about 20 to about 50 μm, and more preferably from about 25 to about 35 μm.

In the present invention, the average particle size of the microspheres may be adjusted in suitable combination with the type of emulsion homogenizer used during PLGA production (e.g., Physcotron (produced by Nichion Irika Kikai Seisakusho), Homo Mixer (produced by Primix Corporation), Uni Mixer (Primix Corporation), TK Robomix (Primix Corporation) etc.) and the rate of rotation during agitation.

As used herein, "average particle size of the inventive microspheres" refers to the average particle size (weight-based mean diameter) of primary particles thereof, and may be measured with, for example, a commonly used laser diffraction-type particle size distribution analyzer (e.g., SALD-2100 (manufactured by Shimadzu Corporation) or a Coulter counter (Multisizer3, manufactured by Beckman Coulter, Inc.). The average particle sizes of microspheres mentioned in this specification are values measured by the Coulter counter method.

In the present invention, the weight ratio of the present drug and the PLGA in the microspheres, expressed as the number of parts by weight of PLGA per part by weight of the drug, is preferably from about 3 to about 10, more preferably from about 3.5 to about 9, and most preferably from about 4 to about 8.

When the encapsulation ratio of the present drug included in the PLGA (the "encapsulation ratio" can be converted to the corresponding content of the present drug) is low, the dose of PLGA increases. Concerning the safety of PLGA itself, in development for use in, e.g., Leuplin injections and Sandostatin LAR intramuscular injections, PLGA has been confirmed to be free of toxicity. It is known that when a large amount is administered, the concentrations of hydrolyzed lactic acid and/or glycolic acid rise at the site of administration, precipitating an acidity problem. Therefore, it is desirable to reduce as much as possible the amount of PLGA at the time of administration; to this end, there is a need to increase the encapsulation ratio of the present drug. On the other hand, when the encapsulation ratio of the present drug is increased, the surface structure of the microsphere particles becomes strained, as a result of which the initial burst rises. Therefore, the encapsulation ratio is preferably from about 9% to about 25% (which corresponds to a drug content where the amount of PLGA per part by weight of the drug is from about 3 to about 10 parts by weight), more preferably from about 10% to about 22% (which corresponds to a drug content where the amount of PLGA per part by weight of the drug is from about 3.5 to about 9 parts by weight), and most preferably from about 11% to about 20% (which corresponds to a drug content where the amount of PLGA per part by weight of the drug is from about 4 to about 8 parts by weight).

In the microspheres of the invention, the content, or encapsulation ratio, of the present drug included in the PLGA is expressed by the following formula.

$$\text{Encapsulation ratio (\%)} = (\text{measured content of drug}/\text{amount of microspheres}) \times 100$$

The encapsulation ratio can be measured by the method described subsequently in the working examples.

In the present invention, "two to four-week, long-acting" microspheres refers to microspheres having the ability to continuous release the drug encapsulated in the microspheres of the invention for a period of from about two weeks to about four weeks following administration. "Two-week, long-acting" or "four-week, long-acting" microspheres refer to the ability to continuously release an effective dose of the drug encapsulated in the microspheres of the invention for a period of about two weeks or about four weeks following administration. Moreover, in the present specification, both the expression "two-week, long-acting" and the expression "having a two-week slow release period" have the same meaning, and both the expression "four-week, long-acting" and the expression "having a four-week slow release period" have the same meaning.

In the present invention, the expression "release the drug at a fixed rate for about four weeks following administration" means that the present drug encapsulated within the microspheres of the invention is released continuously and at a fixed rate, i.e., steadily, for about four weeks following administration. Here, the method of confirming that the present drug is released at a fixed rate, as will be apparent to persons skilled in the art, involves confirming that, in the subsequently described in vitro release test, the remaining ratio of the present drug changes linearly with time; i.e., undergoes zero-order release. By means of this ability, the effective concentration of the present drug in the blood or the effective concentration of the present drug at the site of disease can be continuously and steadily maintained within the above-indicated release period. As noted above, the preferred period of release is two weeks or four weeks.

The blood concentrations of the drug in rats that were obtained in the subsequently described working examples are concentrations suitable for avoiding side effects (e.g., weight loss, diarrhea, hypotensive effects) in the rat, or the like and for manifesting the drug effects. As will be apparent to those skilled in the art, this blood concentration can be extrapolated to the blood concentration of the drug in humans.

When the blood concentration of the present drug in humans exceeds about 150 ng/mL, in addition to a platelet aggregation-inhibiting effect, there is a concern that facial flushing, heavy headedness and a transient hypotensive effect will appear. On the other hand, when the blood concentration and/or local concentration in disease tissue of the present drug is below about 0.01 ng/mL, there is a possibility that the drug effects will not fully appear.

Because blood concentration results obtained from rats are generally extrapolated to humans by using numerical values ranging from about $1/100^{th}$ to about 100 times the blood concentration obtained in rats, the blood concentration of the drug suitable for manifesting drug effects in humans is conjectured to be from about 0.01 ng/mL to about 150 ng/mL.

In the present invention, the expression "to maintain the blood concentration of the drug" means, when the microspheres of the invention are systemically administered, to maintain the blood concentration of the present drug in a range suitable for avoiding side effects and manifesting the drug effects in humans. Such range is preferably from about 0.01 ng/mL to about 150 ng/mL, and more preferably from about 0.1 ng/mL to about 60 ng/mL. In cases where the microspheres of the present drug are administered to the site of disease for the purpose of maintaining the local concentration at a continuously high concentration, the blood concentration of the present drug that flows out into the blood, although dependent also on the site of the organ, etc. to which the microspheres are administered, is typically from about $1/10^{th}$ to about $1/100^{th}$ of the range of from about 0.01 ng/mL to about 150 ng/mL.

The dosage form of the inventive microspheres is exemplified by subcutaneous, intradermal, intramuscular and intravascular injections, injections to the local organ of disease, such as central nervous system or myocardial injections, etc.; embedding agents mixed with bone cement, an artificial bone prosthesis material (β-TCP; tricalcium phosphate) or a gelatin hydrogel, etc.; drug-eluting stents (DES); agents that are administered transmucosally, such as in the rectum, uterine or oral cavity, etc.; oral agents, suppositories, nasal drops, inhalants, eye drops; and administration to the joint cavities or to the focal site etc. such as a tumor etc., or the like.

By holding the remaining ratio of the present drug after one hour to at least about 90% in microspheres having a slow-release period of two weeks, or by holding the remaining ratio of the present drug after one day to at least about 82% in microspheres having a slow-release period of four weeks, an initial burst can be suppressed. In other words, it is possible to suppress the amount of the present drug initially released, to suppress a transient rise in the blood concentration of the drug, and to suppress the hypotensive effect, etc. that accompanies a transient rise in the blood concentration of the drug.

In the present invention, the method of evaluating the degree of initial burst is not subject to any particular limitation. An example of such a method is the in vitro release test described in the subsequent working examples. In the present invention, in such an in vitro release test, it was determined that the initial burst is suppressed in microspheres having a slow-release period of two weeks by holding the remaining ratio of the present drug after one hour to at least about 90%, and in microspheres having a slow-release period of four weeks by holding the remaining ratio of the present drug after one day to at least about 82%.

In the present invention, additives may be included in order to increase the initial burst-suppressing effect. Preferred examples include substances which increase the viscosity of the internal aqueous phase or harden under the effects of temperature or ion addition, substances having basic residues that bear a positive electrical charge, and substances which interact with macromolecular polymers and increase the viscosity of o/w or w/o/w emulsions. Illustrative examples include gelatin, agar, alginic acid, polyvinyl alcohol, polyethylene glycol (PEG) or alginic acid, a basic amino acid such as lysine, etc., polypeptides containing a basic amino acid, organic bases such as N-methylglucamine, etc., or natural or synthetic basic macromolecules (including chitosans such a hydroxypropyltrimonium chitosan, etc.) or the like (at concentrations in the internal aqueous phase of from about 0.05% to about 80%).

Moreover, in the present invention, to increase the initial burst-suppressing effect, PLGA having a low-molecular weight of about 3,000 or less present at the time of microsphere production may be excluded.

Methods for producing the microspheres of the invention are exemplified by drying in water methods (e.g., o/w methods, w/o methods, w/o/w methods, etc.), phase separation methods, spray drying methods, granulation methods using supercritical fluids, methods in general accordance with any of the above, and methods described in the working examples herein, or the like.

Production methods are described in detail below for a drying in water method (o/w method) and a spray drying method.

(1) Drying in Water Method (o/w Method)

In this method, first an organic solvent solution of PLGA or organic solvent/alcohol-type solvent mixed solution of PLGA is prepared. The organic solvent preferably has a boiling point of 120° C. or less. Illustrative examples of the organic solvent include halogenated hydrocarbons (e.g., dichloromethane, chloroform, etc.), aliphatic esters (e.g., ethyl acetate, etc.), ethers, aromatic hydrocarbons, ketones (e.g., acetone, etc.), alcohols (e.g., methanol, ethanol, etc.), aliphatic carboxylic acids (e.g., acetic acid, etc.), dimethylsulfoxide (DMSO) and dimethylformamide (DMF), etc.

Alternatively, two or more of these may be mixed in suitable ratios and used together. The organic solvent is preferably dichloromethane or acetone. Examples of the alcohol-type solvent include methanol, ethanol and propanol, etc. Methanol or ethanol is preferred. The volumetric ratio (v/v) of the organic solvent/alcohol-type solvent is preferably from about 1/1 to about 20/1, and more preferably from about 2/1 to about 10/1.

The concentration of PLGA in the organic solvent solution or in the organic solvent/alcohol-type solvent mixed solution varies according to the weight-average molecular weight of PLGA, the kind of the organic solvent and alcohol-type solvent, or the like, but is generally selected from about 0.01% to about 80% (w/v), preferably from about 0.1% to about 40% (w/v), and more preferably from about 1% to about 20% (w/v).

The present drug is added and dissolved in the organic solvent solution or organic solvent/alcohol-type solvent mixed solution of PLGA thus obtained. The amount of this drug is added varies with such factors as the target release period, etc. but the concentration of PLGA in the organic solvent solution or organic solvent/alcohol-type solvent mixed solution is generally from about 0.001% to about 90% (w/v), preferably from about 0.1% to about 50% (w/v), and more preferably from about 0.3% to about 30% (w/v). Where necessary, antioxidants and/or additives may be dissolved, together with the drug, in the organic solvent solution or organic solvent/alcohol-type solvent mixed solution of PLGA.

Next, the solution prepared as described above is added to an aqueous phase and an oil-in-water emulsion is formed using an agitator, emulsifier or the like. The volume of the aqueous phase at this time is generally from about 1 time to about 10,000 times, preferably from about 2 times to about 5,000 times, and more preferably from about 10 times to about 1,000 times the volume of the oil phase. An emulsifying agent may be added to the aqueous phase. The emulsifying agent may generally be anything that is capable of forming a stable oil-in-water emulsion. Illustrative examples of the emulsifying agent include anionic surfactants, nonionic surfactants, polyoxyethylene castor oil derivatives, polyvinyl pyrrolidone, polyvinyl alcohol, carboxymethyl cellulose, lecithin and gelatin, etc. These may be suitably combined and used. A preferred example of the emulsifying agent is polyvinyl alcohol (PVA). The concentration of the emulsifying agent in the external aqueous phase is preferably from about 0.001% to about 20% (w/v), more preferably from about 0.01% to about 10% (w/v), and most preferably from about 0.05% to about 5% (w/v).

By suitably adjusting the rate of agitation during formation of the oil-in-water emulsion, it is possible to adjust the particle size of the resulting microspheres. For example, at a rapid rate of rotation, the particle size of the microspheres obtained will be smaller; conversely, at a slower rate of rotation, the particle size will be larger.

A commonly used method is employed to evaporate off the solvent of the oil phase. Solvent evaporation may be carried out at normal pressure or under gradual pressure reduction while stirring with, for example, an agitator or a magnetic stirrer, etc., or may be carried out using a rotary evaporator, etc. while adjusting the degree of vacuum. The microspheres thus obtained are collected by centrifugal separation or filtration, then free active ingredient, emulsifying agent and the like adhering to the surfaces of the microspheres are washed off several times with, for example, a surfactant solution or alcohol, following which the microspheres are again dispersed in distilled water (purified water) and freeze-dried. In the above-described oil-in-water method, the microspheres may instead be produced by dispersing the drug in an organic solvent solution of PLGA; i.e., by a s/o/w method. Also, to enhance the dispersibility of the produced microspheres in an injectable solution, suppress agglomeration and thereby obtain a stable, slow-releasing microsphere injection, freeze-drying may be carried out after first adding dispersants, preservatives, tonicity agents, excipients and antioxidants. Adding these additives suppresses the tendency for the microspheres to mutually agglomerate and enhances suspendability, thereby making it possible to improve the ability to pass through a syringe needle.

(2) In cases where the microspheres of the invention are produced by a spray drying process, an organic solvent or emulsion in which the PLGA and the active ingredients are dissolved is sprayed into the drying chamber of a spray dryer using a nozzle, causing the organic solvent or water within the finely divided liquid droplets to evaporate in a very short time, thus producing microspheres. The nozzle may be any of various types, include two-liquid nozzles, four-liquid nozzles, pressurized nozzles and rotary disk nozzles, etc. At this time, if desired, to prevent agglomeration of the microspheres simultaneous with spraying of the oil-in-water emulsion, it is effective to spray an organic solvent or an aqueous solution of an antiflocculant (e.g., mannitol, lactose, gelatin, etc.) from another nozzle. If necessary, for the microspheres thus obtained, the removal of moisture and solvent within the microspheres is carried out more completely under warming and a reduced pressure.

Examples of dispersants include mannitol, lactose, glucose, Tween 80 (trade name), HCO-60 (trade name), CMC-Na (trade name), sodium alginate, starches (e.g., cornstarch, etc.), glycine, fibrin and collagen, etc.

Examples of preservatives include methylparaben and propylparaben, etc.

Examples of tonicity agents include sodium chloride, mannitol, sorbitol and glucose, etc.

Examples of excipients include mannitol, sorbitol, lactose and glucose, etc.

Examples of antioxidants include parabens (e.g., methylparaben, etc.), sorbic acid and salts thereof, butylhydroxyanisole (BHA), dibutylhydroxytoluene (BHT), α-tocopherol, ascorbic acid palmitate, nordihydroxyguaiaretic acid, guaiacol esters, 1,3-butylene glycol, sodium dehydroacetate, propyl gallate, etc.), salts which produce trivalent metal ions (e.g., aluminum chloride, alum, aluminum allantoinate).

Because the microspheres containing the present drug and PLGA, described in Preparation Example 2 of International Patent Publication WO 2004/032965 pamphlet have a very low drug content of about 5%, a large amount must be administered to obtain sufficient drug effects. As a result, the amount of PLGA itself administered also increases, which may give rise, as mentioned above, to acidity problems following administration. In the present invention, the drug content (encapsulation ratio) was increased in order to overcome the foregoing problem. However, simple increase of the drug content leads, as indicated in the subsequent examples, to the occurrence of an initial burst of the drug. For this reason, by also suitably adjusting and combining the weight-average molecular weight of the PLGA, the lactic acid/glycolic acid ratio in the PLGA, the average particle size of the microspheres and the weight ratio of the drug and the PLGA, microspheres which suppress an initial burst of the drug and are able to achieve release of the drug at a fixed rate (zero-order release) over a period of from about two weeks to about four weeks following administration were discovered. It was also discovered that the microspheres of the invention are able, during the period of slow-release, to avoid side effects and to maintain the blood concentration of the drug within a range that is optimal for manifesting drug effects.

In the present invention, to produce microspheres having a slow-release period of from about two weeks to about four weeks and having the above-described features, it is preferable to (1) set the average particle size of the microspheres to from about 20 to about 50 µm, (2) set the amount of lactic acid/glycolic acid copolymer per part by weight of the drug to from about 3 to about 10 parts by weight, and (3) set the weight-average molecular weight of the lactic acid/glycolic acid copolymer to from about 10,000 to about 50,000 and set the lactic acid/glycolic acid ratio to from about 75/25 to about 50/50; and it is even more preferable to (1) set the average particle size of the microspheres to from about 25 to about 35 µm, (2) set the amount of lactic acid/glycolic acid copolymer per part by weight of the drug to from about 4 to about 8 parts by weight, and (3) set the weight-average molecular weight of the lactic acid/glycolic acid copolymer to from about 10,000 to about 50,000 and set the lactic acid/glycolic acid ratio to about 50/50.

Of the above, to produce microspheres having a slow-release period of two weeks, (1) the average particle size of the microspheres is set to from about 25 to about 35 µm, (2) the amount of lactic acid/glycolic acid copolymer per part by weight of the drug is set to from about 4 to about 8 parts by weight, and (3) the weight-average molecular weight of the lactic acid/glycolic acid copolymer is set to from about 10,000 to about 20,000 and the lactic acid/glycolic acid ratio is set to about 50/50. To produce microspheres having a slow-release period of four weeks, (1) the average particle size of the microspheres is set to from about 25 to about 35 µm, (2) the amount of lactic acid/glycolic acid copolymer per part by weight of the drug is set to from about 4 to about 8 parts by weight, and (3) the weight-average molecular weight of the lactic acid/glycolic acid copolymer is set to from about 50,000 and the lactic acid/glycolic acid ratio is set to about 50/50.

As mentioned above with regard to the microspheres of the invention wherein each of the constituent conditions have been set within the preferred ranges, in the in vitro release tests described in the subsequent examples, because the microspheres with a slow-release period of two weeks have a remaining ratio of the drug after one hour from administration, of at least about 90% and the microspheres with a slow-release period of four weeks have a remaining ratio of the drug after one day from administration, of at least about 82%, both suppress an initial burst. In addition, as shown in the subsequent examples, the above microspheres also have the ability to maintain an effective blood concentration for the respective slow-release periods.

[Applications as Pharmaceutical Preparations]

The present drug has a $PGI_2$ receptor agonist action, a $TXA_2$ synthetase inhibiting action, an endogenous repair factor production promoting action, a stem cell differentiation inducing action and an angiogenesis accelerating action, etc., and therefore, this drug and microspheres containing this drug are useful as preventive and/or therapeutic agents for various types of organ disorders, including diseases of the blood and lymph vessels (e.g., arteriosclerosis obliterans (ASO), Buerger disease, Raynaud disease, arteriosclerosis, lymphedema, etc.), heart disease (e.g., myocardial infarction, angina, ventricular tachyarrhythmia, congestive heart failure, coronary artery disease, idiopathic cardiomyopathy, dilated cardiomyopathy, atrial fibrillation, myocarditis, etc.), nerve degeneration diseases (e.g., ischemic encephalopathy, cerebrovascular accidents, stroke (cerebral infraction, cerebral hemorrhage, etc.), Parkinson disease, Alzheimer disease, diabetic neuropathy, spinal canal stenosis, dementia, moyamoya disease, spinal cord injuries, amyotrophic lateral sclerosis (ALS), cerebral aneurysm, etc.), lung diseases (e.g., acute pneumonia, pulmonary fibrosis, pulmonary hypertension, chronic obstructive pulmonary disease (COPD), systemic inflammatory response syndrome (SIRS), acute lung injury (ALI), acute respiratory distress syndrome (ARDS), sarcoidosis, interstitial pneumonia, hypersensitivity pneumonitis, asthma, etc.), bone/cartilage disease (e.g., osteoarthritis (OA) of the vertebra or knee, etc., rheumatoid arthritis (RA), osteoporosis, bone fracture, osteonecrosis, periosteal injury, sternum regeneration therapy associated with cardiopulmonary surgery, etc.), liver diseases (e.g., fulminant hepatitis, acute hepatitis, cirrhosis, chronic hepatitis, fatty liver, etc.), kidney diseases (e.g., acute renal failure, ischemic renal disorder, crush syndrome, necrotic renal failure, glomerular disease, glomerulonephritis, nephrosclerosis, proliferative glomerulonephritis, tubulointerstitial disease, renovascular disorders, cystic kidney disease, toxic nephropathy, tubular transport abnormalities, renal disorders in dialysis patients, nephropathy, etc.), pancreatic diseases (e.g., diabetes, chronic pancreatitis, acute pancreatitis, etc.), digestive tract diseases (e.g., esophagitis, gastritis, gastric ulcer, duodenal ulcer, inflammatory bowel disease, ulcerative colitis, Crohn disease, etc.), organ/tissue transplants (heart transplant, liver transplant, kidney transplant, lung transplant, pancreas transplant, myocutaneous flap transplant, esophagus transplant, skin transplant, blood/lymph vessel transplant, hemopoietic stem cell transplant, bone/cartilage transplant, etc.), diabetic complications (e.g., nerve disorders, skin ulcers, nephropathy, etc.), vascular endothelial cell disorders (e.g., prevention of restenosis after PTCA (percutaneous transluminal coronary angioplasty, etc.), dental diseases (e.g., periodontal disease, tooth extraction wounds, wounds of the oral cavity, periodontal bone tissue disorders, periodontitis, etc.), skin diseases (e.g., bed sores, alopecia disease, alopecia areata, skin ulcers, etc.), ophthalmic diseases (e.g., glaucoma, etc.), diseases of the ears and nose (e.g., deafness, sensorineural deafness, etc.), multiple organ failure (MOF), allergic diseases and collagen disease, or the like. The present drug and microspheres containing it are especially promising as an agent for preventing and/or treating the following blood/lymph vascular diseases: ASO, Buerger disease, lymphedema and diabetic ulcers; the following heart diseases: myocardial infarction, angina and heart failure; the following lung diseases: pulmonary fibrosis, pulmonary hypertension, asthma and COPD; the following kidney diseases: acute renal failure, chronic renal failure and diabetic nephropathy; the following bone/cartilage diseases: OA, RA, osteoporosis, bone fractures; the following nerve degeneration diseases: stroke, Parkinson disease, spinal cord injuries and diabetic nerve disorders; and the following liver diseases: acute hepatitis, fulminant hepatitis, cirrhosis and PTCA restenosis.

The endogenous repair factor whose production the present drug induces, promotes or amplifies varies depending on the production cells, and is known to include, for example: vascular endothelial growth factor (VEGF), hepatocyte growth factor (HGF), various fibroblast growth factors (a/b FGF), transformation growth factor-α/β (TGF-α/β), platelet-derived growth factor (PDGF), angiopoietin, hypoxia-inducing factor (HIF), insulin-like growth factor (IGF), bone morphogenetic protein (BMP), connective tissue growth factor (CTGF), epidermal growth factor (EGF), nerve growth factor (NGF), brain-derived neurotrophic factor (BDNF), glia cell-derived neurotrophic factor (GDNF), stem cell factor (SCF), granulocyte colony-stimulating factor (G-CSF), connective tissue growth factor (CTGF), granulocyte-macrophage colony-stimulating factor (GM-CSF), keratinocyte growth factor (KGF), chondrocyte growth factor (GDF), and related families of growth factors. In the course of the present investigations, a new, stroma cell-derived factor (SDF-1) production-inducing action has been discovered. It has been found that SDF-1 is a cytokine which is not limited only to hemopoiesis, but serves as a key to regulation of the kinetics of stem cells and precursor cells in the course of development. For example, the present drug induces the production of VEGF-A, HGF, EGF and SDF-1 from fibroblasts. Other drugs that produce the above-mentioned endogenous repair factors include other prostaglandin (PG) $I_2$ receptor agonists (e.g., beraprost, iloprost, NS-304, etc.), EP2 and EP4 receptor (both of which are $PGE_2$ receptors) agonists, and mixtures of these agonists (e.g., PGE1, PGE2, PGI2 and derivatives thereof, etc.). To achieve the objects of the present invention, the above-mentioned drugs may be used instead of the present drug.

The microspheres of the invention, when administered subcutaneously, intramuscularly and/or by tissue implantation, are slowly released over an extended period of time, thereby maintaining the local tissue concentration and/or blood concentration of the drug. The drug whose concentration is thus maintained increases blood flow in the remaining blood vessels by, for example, vasodilative effects and platelet aggregation-inhibiting activity, etc., due to the inherent $PGI_2$ receptor agonist activity and $TXA_2$ synthetase inhibiting activity, etc. Also, because the present drug promotes the production of various endogenous repair factors, it has a tissue regeneration-promoting effect due to, for example, a vascularization/regeneration-promoting activity and a stem cell differentiation-inducing activity, and thus has selective effects on a variety of diseases.

The release period and method of administration are suitably selected according to the disease and method of treatment thereof while taking into account such considerations as safety, convenience, low invasiveness, the burden on the patient, and compliance, or the like.

Because the microspheres of the invention have a slow-release period of from about two weeks to about four weeks, of the above-mentioned diseases, they are particularly useful for preventing and/or treating diseases of the blood/lymph vessels (e.g., ASO, Buerger disease, Raynaud disease, lymphedema, preventing PTCA restenosis, etc.), heart disease (e.g., myocardial infarction, angina, heart failure, dilated cardiomyopathy, etc.), kidney diseases (e.g., acute renal failure, chronic renal failure, diabetic nephropathy, etc.), nerve degeneration diseases (e.g., stroke, Parkinson disease, diabetic neuropathy, spinal cord injuries, etc.), lung diseases (e.g., pulmonary hypertension, pulmonary fibrosis, asthma, COPD, etc.), and bone/cartilage diseases (e.g., osteoporosis, rheumatoid arthritis, osteoarthritis, bone fractures, periodontal disease, etc.).

Preferred methods of administration for use of the microspheres of the invention on these diseases include direct administration to the site of disease by techniques that entail inclusion in an injection administered subcutaneously, intradermally, intramuscularly, intravascularly, or locally into the tissue at the site of disease, such as the central nervous system or the cardiac muscle; in an embedding agent mixed with bone cement, artificial bone prosthesis material (β-TCP; tricalcium phosphate), gelatin hydrogels or the like; and in suture thread, bolts, films or sheets; and methods that involve coating onto a stent or the like. In addition, administration may be carried out in the form of an agent given transmucosally in the rectum, uterus, oral cavity, etc.; as an oral agent, suppository, nasal drops, inhalant, eye drops; to an articular cavity; percutaneously, as an ointment, or as adhesive skin patches; or to the site of disease such as a tumor.

[Toxicity]

The present drug and the microspheres of the invention have a low toxicity and are sufficiently safe for use as medications.

Effect of the Invention

The present drug and the microspheres of the invention are useful for preventing and/or treating cardiac diseases, blood/lymph vessel diseases, lung diseases, kidney diseases, liver diseases, pancreatic diseases, bone/cartilage diseases, allergies and nerve degeneration diseases. Because the microspheres of the invention release the present drug at a fixed rate over a period of from about two weeks to about four weeks following administration, they are particularly useful for preventing and/or treating ASO, myocardial infarction, angina, stroke, diabetes and complications thereof, renal failure, pulmonary fibrosis, pulmonary hypertension, asthma, OA, RA and osteoporosis. Moreover, the microspheres of the invention suppress an initial burst of the present drug and, for a period of from about two weeks to about four weeks following administration, are able to maintain the blood concentration of the drug in a range that avoids side effects and is suitable for manifesting the drug effects.

BEST MODE FOR CARRYING OUT THE INVENTION

Figure 1:
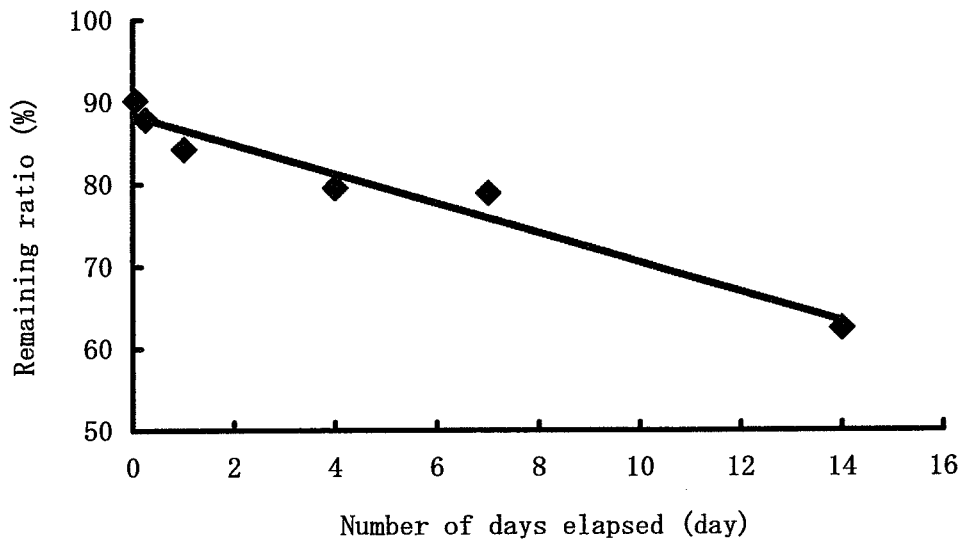
FIG. 1 shows, in an in vitro release test, the change over time in the remaining ratio of the drug in the microspheres prepared in Preparation Example 1-4.

The present invention is illustrated more fully below in preparation examples and working examples. However, the invention is not limited by these examples.

Preparation Example 1

Preparation of Microspheres (o/w Method)

The present drug and PLGA were dissolved in dichloromethane or a mixed solution of dichloromethane and methanol (or dimethylsulfoxide, acetic acid). The resulting solution was added to from 300 mL to 40,000 mL of an aqueous solution (adjusted to pH 3.0 with 1N hydrochloric acid) of 0.1% polyvinyl alcohol (produced by nacalai tesque) agitated at from 1,000 to 5,000 rpm using a Physcotron (NS-60, manufactured by Nichion Irika Kikai Seisakusho), following which the mixture was agitated at room temperature for a period of from 30 seconds to 3 minutes to form an oil-in-water emulsion. The oil-in-water emulsion was agitated at room temperature for 4 hours to evaporate the dichloromethane and solidify the oil phase, which was then centrifuged (3,000 rpm, 10 minutes) using a centrifuge (HIMAC-CR5B2, manufactured by Hitachi, Ltd.). The supernatant was discarded, the residue was dispersed in purified water (30 to 50 mL), and the dispersion was centrifuged (3,000 rpm, 10 minutes). The supernatant was again discarded, the residue was dispersed in a 0.2% (w/v) Tween solution (30 to 50 mL), and the dispersion was centrifuged (3,000 rpm, 10 minutes). The supernatant was once again discarded, following which the residue was again dispersed with purified water (30 mL), the resulting dispersion was centrifuged (3,000 rpm, 10 minutes), and the supernatant was discarded. The precipitate was frozen with dry ice-methanol, then dried under reduced pressure (12 hours), thereby producing microspheres of the present drug. In Preparation Example 1-3, PLGA-5010 from which the low molecular weight components (having weight-average molecular weights of 1 to 3,000) had been cut off by a known method was used as the PLGA.

The average particle size of the resulting microspheres was measured using a Coulter counter (Multisizer3, manufactured by Beckman Coulter).

In addition, the content of the present drug (encapsulation ratio) in the resulting microspheres was measured by the following method.

The microspheres (approx. 10 mg) produced as described above were added to 50 mL of acetonitrile and ultrasonic treatment was carried out for 10 minutes, thereby dissolving the microspheres. Next, 100 μL of an internal standard (IS) solution A and 500 μL of a mobile phase (pH 3.0) were added to and intimately mixed with 400 μL of the solution prepared as described above. The resulting mixed solution was centrifuged (12,000 rpm, 3 minutes), and the content of the present drug present in 10 μL of the resulting supernatant was measured by high-performance liquid chromatography (HPLC), based on which the encapsulation ratio of the drug in the microspheres was calculated.

Encapsulation Ratio (%)=(measured content of drug/amount of microspheres)×100

HPLC Conditions

Apparatuses: Chromatograph (Shimadzu LC-10AT; manufactured by Shimadzu Corporation), UV detector (Shimadzu SPD-10A: Shimadzu Corporation), data analyzer (Shimadzu C-R7A; Shimadzu Corporation).

Detection: UV-265 nm

Column: SHISEIDO CAPCELLPACK C18 UG120 (4.6 mm i.d.×150 mm); manufactured by Shiseido Co., Ltd.

Column temperature: constant temperature of close to 25° C.

Mobile Phase Acetonitrile: water: triethylamine=1000:900:3 (a mixed solution of water and triethylamine is adjusted to pH 3 with phosphoric acid)

Flow Rate: 1.0 mL/min

Internal Standard (IS): n-propylparaben

Drug Elution Time: 7 minutes

IS Elution Time: 4 minutes

IS Solution A Preparation Method

First, 100 mg of the Internal Standard was weighed out and brought up to 100 mL with ethanol. Ten milliliters of the resulting solution was then brought up to 100 mL with ethanol. The resulting solution was used as IS solution A.

The results of the above preparations and measurements are shown in the following Tables 1 to 4. In the tables below, "PL/GA" refers to the polylactic acid (PL)/glycolic acid (GA) ratio in the PLGA. The rotational speed refers to the rotational speed when the mixed solution containing the present drug and PLGA and the 0.1% polyvinyl alcohol aqueous solution are agitated using a Physcotron to produce an oil-in-water emulsion. $CH_2Cl_2$ refers to dichloromethane, MeOH refers to methanol, and DMSO refers to dimethylsulfoxide.

TABLE 1

| Comparative Preparation Example | Amount of present drug | PLGA type (amount) | PLGA weight-average molecular weight | PL/GA | Amount of solvent | Average particle size (μm) | Encapsulation Ratio (%) |
|---|---|---|---|---|---|---|---|
| 1-1 | 15 mg | PLGA-5020 (50 mg) | 20,000 | 50/50 | $CH_2Cl_2$ (3 mL) | 13.2 | 24.3 |
| 1-2 | 20 mg | PLGA-5020 (50 mg) | 20,000 | 50/50 | $CH_2Cl_2$ (4 mL) | — | 33.0 |
| 1-3 | 25 mg | PLGA-5020 (50 mg) | 20,000 | 50/50 | $CH_2Cl_2$ (5 mL) | — | 45.6 |
| 1-4 | 133 mg | PLGA-5020 (200 mg) | 20,000 | 50/50 | $CH_2Cl_2$ (5 mL) MeOH (2.5 mL) | 13.4 | 37.7 |
| 1-5 | 133 mg | PLGA-5020 (200 mg) | 20,000 | 50/50 | $CH_2Cl_2$ (5 mL) MeOH (2.5 mL) | 14.2 | 38.6 |
| 1-6 | 200 mg | PLGA-5020 (200 mg) | 20,000 | 50/50 | $CH_2Cl_2$ (5 mL) MeOH (2.5 mL) | 14.5 | 50.0 |
| 1-7 | 164 mg | PLGA-5020 (200 mg) | 20,000 | 50/50 | $CH_2Cl_2$ (5 mL) MeOH (2.5 mL) | 14.5 | 45.4 |

TABLE 2

| Comparative Preparation Example | Amount of present drug | PLGA type (amount) | PLGA weight-average molecular weight | PL/GA | Amount of solvent | Average particle size (μm) | Encapsulation Ratio (%) |
|---|---|---|---|---|---|---|---|
| 2-1 | 20 mg | PLGA5-50 (100 mg) | 50,000 | 50/50 | $CH_2Cl_2$ (1 mL) MeOH (0.5 mL) | 38.2 | 15.3 |
| 2-2 | 270 mg | PLGA5-50 (500 mg) | 50,000 | 50/50 | $CH_2Cl_2$ (7 mL) MeOH (2.5 mL) | 19.5 | 31.5 |
| 2-3 | 200 mg | PLGA5-50 (200 mg) | 50,000 | 50/50 | $CH_2Cl_2$ (5 mL) MeOH (2.5 mL) | 17.4 | 48.6 |
| 2-4 | 164 mg | PLGA5-50 (200 mg) | 50,000 | 50/50 | $CH_2Cl_2$ (5 mL) MeOH (2.5 mL) | 16.6 | 42.1 |
| 2-5 | 133 mg | PLGA5-50 (200 mg) | 50,000 | 50/50 | $CH_2Cl_2$ (5 mL) MeOH (2.5 mL) | 16.6 | 36.3 |

TABLE 2-continued

| Comparative Preparation Example | Amount of present drug | PLGA type (amount) | PLGA weight-average molecular weight | PL/GA | Amount of solvent | Average particle size (μm) | Encapsulation Ratio (%) |
|---|---|---|---|---|---|---|---|
| 2-6 | 200 mg | PLGA5-50 (200 mg) | 50,000 | 50/50 | CH$_2$Cl$_2$ (5 mL) MeOH (2.5 mL) | 19.0 | 49.1 |
| 2-7 | 164 mg | PLGA5-50 (200 mg) | 50,000 | 50/50 | CH$_2$Cl$_2$ (5 mL) MeOH (2.5 mL) | 16.6 | 41.1 |
| 2-8 | 133 mg | PLGA5-50 (200 mg) | 50,000 | 50/50 | CH$_2$Cl$_2$ (5 mL) MeOH (2.5 mL) | 16.9 | 36.8 |

TABLE 3

| Preparation Example | Amount of present drug | PLGA type (amount) | PLGA weight-average molecular weight | PL/GA | Amount of solvent | Average particle size (μm) | Encapsulation Ratio (%) |
|---|---|---|---|---|---|---|---|
| 1-1 | 20 mg | PLGA-5020 (100 mg) | 20,000 | 50/50 | CH$_2$Cl$_2$ (1 mL) MeOH (0.2 mL) | 30.0 | 15.9 |
| 1-2 | 110 mg | PLGA-5010 (500 mg) | 10,000 | 50/50 | CH$_2$Cl$_2$ (5 mL) MeOH (2.5 mL) | 28.0 | 17.3 |
| 1-3 | 110 mg | PLGA-5010 (500 mg) | 10,000 | 50/50 | CH$_2$Cl$_2$ (5 mL) MeOH (2.5 mL) | 30.6 | 16.4 |
| 1-4 | 110 mg | PLGA-5020 (500 mg) | 20,000 | 50/50 | CH$_2$Cl$_2$ (5 mL) MeOH (2.5 mL) | 27.8 | 16.5 |

TABLE 4

| Preparation Example | Amount of present drug | PLGA type (amount) | PLGA weight-average molecular weight | PL/GA | Amount of solvent | Average particle size (μm) | Encapsulation Ratio (%) |
|---|---|---|---|---|---|---|---|
| 2-1 | 20 mg | PLGA5-50 (100 mg) | 50,000 | 50/50 | CH$_2$Cl$_2$ (1 mL) MeOH (0.5 mL) | 31.2 | 14.8 |
| 2-2 | 250 mg | PLGA5-50 (1000 mg) | 50,000 | 50/50 | CH$_2$Cl$_2$ (10 mL) MeOH (2 mL) | 30.3 | 14.9 |
| 2-3 | 3320 mg | PLGA5-50 (13300 mg) | 50,000 | 50/50 | CH$_2$Cl$_2$ (132.9 mL) MeOH (53.1 mL) | 31.7 | 16.5 |
| 2-4 | 44 mg | PLGA5-50 (200 mg) | 50,000 | 50/50 | CH$_2$Cl$_2$ (2 mL) MeOH (1 mL) | 35.0 | 16.4 |
| 2-5 | 35 mg | PLGA5-50 (200 mg) | 50,000 | 50/50 | CH$_2$Cl$_2$ (2 mL) MeOH (1 mL) | 34.8 | 12.2 |

Example 1

In Vitro Release Test

The microspheres produced in Preparation Example 1 were added to a 0.2% (w/v) Tween 80-containing 1/15 M phosphate buffer (pH 7) in such a way as to set the concentration of the present drug to 30 μg/mL, then uniformly dispersed by vortexing (10 seconds) and sonication (20 seconds). The dispersion was dispensed in 1 mL portions to containers and held at rest in a 37° C. incubator. Each container was sampled over time and centrifuged (12,000 rpm, 5 min), the supernatant was discarded and the resulting pellet was frozen with dry ice-methanol and dried under reduced pressure. Next, 500 μL of acetonitrile was added to these pellets and the microspheres were dissolved by ultrasonic treatment. To this solution was added and intimately mixed 500 μL of IS solution B. Next, 500 μL of this mixed solution was weighed out, diluted with 500 μL of mobile phase (pH 3), and centrifuged (12,000 rpm, 3 min), following which the remaining amount of the drug present within the microspheres in 10 μL of the resulting supernatant was measured by HPLC.

The remaining ratio (%) of the present drug was calculated by taking the drug concentration when all of the drug has eluted out (30 μg/mL) to be 100%.

As mentioned above, in microspheres having a slow-release period of two weeks, an initial burst is considered to have been suppressed if the remaining ratio of the drug after one hour is at least 90%. Similarly, in microspheres having a slow-release period of four weeks, an initial burst is considered to have been suppressed if the remaining ratio of the drug after one day is at least 82%.

HPLC Conditions

Apparatuses: Chromatograph (Shimadzu LC-10AT; manufactured by Shimadzu Corporation), UV detector (Shimadzu SPD-10A: Shimadzu Corporation), data analyzer (Shimadzu C-R7A; Shimadzu Corporation).

Detection: UV-265 nm

Column: SHISEIDO CAPCELLPACK C18 UG120 (4.6 mm i.d.×150 mm); manufactured by Shiseido Co., Ltd.

Column temperature: constant temperature of close to 25° C.

Mobile Phase Acetonitrile: water: triethylamine=1000:900:3 (a mixed solution of water/triethylamine (900:3) is adjusted to pH 3 with phosphoric acid)

Flow Rate: 1.0 mL/min

Internal Standard (IS): n-propylparaben

IS Solution B Preparation Method

First, 100 mg of the Internal Standard was weighed out and brought up to 100 mL with ethanol. Ten milliliters of the resulting solution was then brought up to 100 mL with ethanol. Ten milliliters of the latter solution was again brought up to 100 mL with ethanol. The resulting solution was used as IS solution B.

The calculated results are shown below in Tables 5 to 8.

TABLE 5

| Comparative Preparation example | Remaining ratio (%) | | | | | | | |
|---|---|---|---|---|---|---|---|---|
| | 1 hour | 6 hours | 1 day | 4 days | 7 days | 10 days | 14 days | 17 days |
| 1-1 | 73.5 | 58.1 | 38.0 | 18.1 | 16.1 | 14.1 | 7.9 | 2.6 |
| 1-2 | 36.2 | 30.7 | 11.6 | 1.7 | 1.1 | 1.3 | 1.0 | — |
| 1-3 | 8.9 | 2.0 | 1.0 | 0.9 | — | — | — | — |
| 1-4 | 45.2 | 41.7 | 47.8 | — | — | — | — | — |
| 1-5 | 52.8 | 40.5 | 46.9 | — | — | — | — | — |
| 1-6 | 54.0 | 46.9 | 50.5 | — | — | — | — | — |
| 1-7 | 50.3 | 44.7 | 46.8 | — | — | — | — | — |

TABLE 6

| Preparation example | Remaining ratio (%) | | | | | | | |
|---|---|---|---|---|---|---|---|---|
| | 1 hour | 6 hours | 1 day | 4 days | 7 days | 10 days | 14 days | 17 days |
| 1-1 | 91.9 | 88.6 | 83.5 | 85.4 | 79.5 | 58.9 | 36.6 | — |
| 1-2 | 90.5 | 85.4 | 87.3 | 83.1 | 78.5 | — | 75.1 | — |
| 1-3 | 94.3 | 88.8 | 88.8 | 83.6 | 76.2 | — | 71.7 | — |
| 1-4 | 90.2 | 87.9 | 84.3 | 79.6 | 78.9 | — | 62.5 | — |

From the results in Table 5, because the microspheres obtained in Comparative Preparation Examples 1-1 to 1-7 had a small average particle size and/or a high encapsulation ratio, in each case, the remaining ratio of the drug after one hour was less than 90%, indicating that an initial burst has occurred. By contrast, from the results of Table 6, the microspheres obtained in Preparation Examples 1-1 to 1-4 had a remaining ratio of the present drug after one hour of at least 90%, indicating that an initial burst has been suppressed. Also, the microspheres obtained in Preparation Examples 1-1 to 1-4 achieve a sustained release of the present drug for about two weeks. Moreover, as can be seen in FIG. 1, which shows the time course in the remaining ratio of the drug in Preparation Example 1-4, the remaining ratio of the present drug decreases linearly over time, meaning that zero-order release is achieved.

TABLE 7

| Comparative Preparation example | Remaining ratio (%) | | | | | | | |
|---|---|---|---|---|---|---|---|---|
| | 1 hour | 6 hours | 1 day | 7 days | 14 days | 21 days | 28 days | 35 days |
| 2-1 | — | — | 81.5 | 81.3 | 83.7 | 60.4 | 37.7 | 5.8 |
| 2-2 | 83.2 | 82.6 | 81.5 | 75.6 | 70.4 | — | 43.2 | — |
| 2-3 | 59.2 | 45.5 | 46.9 | — | — | — | — | — |
| 2-4 | 53.8 | 40.6 | 47.6 | — | — | — | — | — |
| 2-5 | 45.8 | 35.3 | 38.8 | — | — | — | — | — |
| 2-6 | 55.1 | 43.3 | 54.5 | — | — | — | — | — |
| 2-7 | 54.5 | 41.3 | 49.5 | — | — | — | — | — |
| 2-8 | 54.5 | 41.3 | 49.5 | — | — | — | — | — |

TABLE 8

| Preparation example | Remaining ratio (%) | | | | | | | |
|---|---|---|---|---|---|---|---|---|
| | 1 hour | 6 hours | 1 day | 7 days | 14 days | 21 days | 28 days | 35 days |
| 2-1 | — | — | 92.8 | 85.3 | 72.1 | 53.7 | 22.6 | 1.3 |
| 2-2 | — | — | 82.0 | 72.8 | 40.4 | 10.9 | 10.2 | — |
| 2-3 | 90.7 | — | 84.0 | 78.2 | 66.0 | 50.1 | 10.1 | 4.5 |
| 2-4 | 85.4 | 89.8 | 85.3 | — | — | — | — | — |
| 2-5 | 86.7 | 93.5 | 90.4 | — | — | — | — | — |

Figure 2:
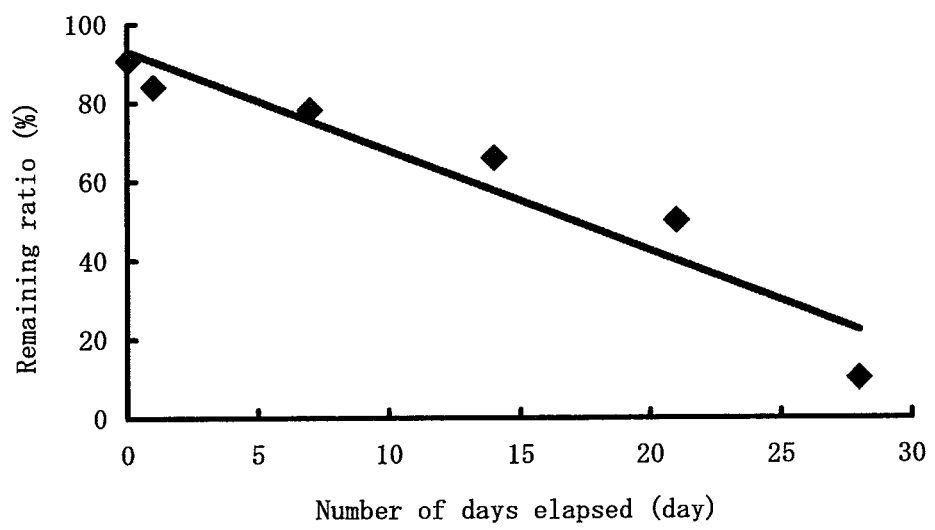
FIG. 2 shows, in an in vitro release test, the change over time in the remaining ratio of the drug in the microspheres prepared in Preparation Example 2-3.

From the results in Table 7, because the microspheres obtained in Comparative Preparation Examples 2-1 to 2-8 had a small average particle size and/or a high encapsulation ration, the remaining ratio of the present drug after one day was less than 82% in each case, indicating that an initial burst has occurred. By contrast, from the results in Table 8, the microspheres obtained in Preparation Examples 2-1 to 2-5 had a remaining ratio of the present drug after one day of at least 82%, indicating that an initial burst has been suppressed. Also, the microspheres obtained in Preparation Examples 2-1 to 2-5 achieve a sustained release of the present drug for about four weeks. Moreover, as can be seen in FIG. 2, which shows the time course of the remaining ratio of the drug in Preparation Example 2-3, the remaining ratio of the present drug decreases linearly over time, meaning that zero-order release is achieved.

It was found that the microspheres having a two-week release period, by being prepared so that (1) the microspheres had an average particle size of from about 25 to about 35 μm, (2) the amount of lactic acid/glycolic acid copolymer per part by weight of the drug was from about 4 to about 8 parts by weight and (3) the lactic acid/glycolic acid copolymer had a weight-average molecular weight of from about 10,000 to about 20,000 and a lactic acid/glycolic acid ratio of about 50/50, were able to release the present drug at a constant rate. In addition, it was found that the microspheres having a four-week release period, by being prepared so that (1) the microspheres had an average particle size of from about 25 to about 35 μm, (2) the amount of lactic acid/glycolic acid copolymer per part by weight of the drug was from about 4 to about 8 parts by weight and (3) the lactic acid/glycolic acid copolymer had a weight-average molecular weight of about 50,000 and a lactic acid/glycolic acid ratio of about 50/50, were able to release the present drug at a constant rate.

Example 2

Blood Concentration Measurement Test

Male Crl:CD (Sprague-Dawley) rats (SPF; Charles River Japan; 8-week-old) were subcutaneously administered the various preparations (microspheres) shown in Table 9 below at a dose of 5 mL/kg under non-fasting conditions. Using three animals from each group (6 animals from each of Test Groups 5 and 6), about 0.5 mL of heparinized blood was collected under unanesthetized conditions from the rat carotid artery at various blood sampling points (3 hours, 8 hours, 24 hours (1 day), 3 days, 7 days, 10 days, 14 days, 17 days, 21 days, 24 days, 28 days following administration). The blood thus obtained was centrifuged at 12,000 rpm for 2 minutes, and the supernatant was collected as plasma.

Blood concentration measurements of the present drug in the resulting plasma were carried out by a LC/MS/MS method. Pretreatment of the plasma consisted of adding an internal standard solution to the plasma and diluting with water, then loading into a solid-phase extraction cartridge column (ODS-B) and deproteinization by rinsing with water, followed by elution with methanol, concentration, and drying to hardness. The residue thus obtained was dissolved by adding 0.1% aqueous acetic acid/acetonitrile, and the resulting solution was poured into the LC/MS/MS apparatus.

HPLC Conditions
HPLC: Shimadzu 10A
Column: CAPCELLPAK C18MG120 (2.0 mm i.d.×150 mm; 5 µm; Shiseido)
Mobile phase: 0.1% aqueous acetic acid/acetonitrile (50:50, vol %)
Flow rate: 0.2 mL/min
MS/MS Conditions
MS/MS: API4000
Ionization mode: ESI
Ion polarity mode: positive
Monitor ions:
  Present drug (Precursor ion (m/z)*: 429.2; Product ion (m/z)*: 79.2)
  Internal standard (Precursor ion (m/z)*: 445.4; Product ion (m/z)*: 168.1)
  *: Mass-to-charge ratio
Retention time for present drug: 8.15 minutes Test Group 1: Microspheres of Test Preparation 1 were administered subcutaneously at a dose of the present drug of 10 mg/kg.
Test Group 2: Microspheres of Test Preparation 2 were administered subcutaneously at a dose of the present drug of 10 mg/kg.
Test Group 3: Administered subcutaneously at a dose of the present drug of 10 mg/kg.
Test Group 4: Administered orally at a dose of the present drug of 10 mg/kg.

The test preparations used on the respective dose groups were formulated as shown below in Table 9. Each of the test preparations was prepared in general accordance with the method described in Preparation Example 1.

TABLE 9

| | Formulated amounts | | | | | |
|---|---|---|---|---|---|---|
| Test preparation | Amount of present drug | PLGA type (amount) | PLGA weight-average molecular weight | PL/GA | Average particle size (µm) | Encapsulation Ratio (%) |
| 1 | 3320 mg | PLGA5-50 (13300 mg) | 50,000 | 50/50 | 31.7 | 16.5 |
| 2 | 110 mg | PLGA-5020 (500 mg) | 20,000 | 50/50 | 28.6 | 16.3 |

The change over time in the blood concentrations of the present drug in each of the test groups are shown below in Tables 10 and 11.

TABLE 10

| | Blood concentration of present drug (ng/mL) | | | | | | | | | | |
|---|---|---|---|---|---|---|---|---|---|---|---|
| Test group | 3 hours | 8 hours | 1 day | 3 days | 7 days | 10 days | 14 days | 17 days | 21 days | 24 days | 28 days |
| 1 | 279.27 | 57.91 | 6.11 | 2.80 | 1.16 | 1.79 | 11.36 | 21.83 | 6.89 | 2.08 | 0.73 |
| 2 | 274.80 | 80.49 | 5.25 | 3.97 | 26.87 | 27.95 | 8.41 | 2.28 | 0.26 | 0.10 | 0.05 |

TABLE 11

| | Blood concentration of present drug (ng/mL) | | | | | | | |
|---|---|---|---|---|---|---|---|---|
| Test group | 1 hour | 2 hours | 4 hours | 8 hours | 12 hours | 1 day | 2 days | 3 days |
| 3 | 1754.12 | 1398.18 | 685.49 | 870.43 | 204.29 | 1.05 | 0.15 | 0.05 |
| 4 | 784.72 | 981.55 | 1321.64 | 705.03 | — | 79.96 | 0.05 | 0.04 |

As is apparent from the above results, the subcutaneous administration (Test Group 3) and oral administration (Test Group 4) of the present drug showed high blood concentrations from 1 hour until 8 hours after administration; two days after administration, the blood concentration was below 0.2 ng/mL. By contrast, of the microspheres of the present invention, in Test Group 1 having a four-week slow release period, the blood concentration of the drug was continuously maintained during the period from 1 day to 28 days following administration within a range of from about 0.7 ng/mL to about 22 ng/mL. Similarly, in Test Group 2 having a two-week slow release period, the blood concentration of the drug was continuously maintained during the period from 1 day to 14 days following administration within a range of from about 4 ng/mL to about 30 ng/mL. Moreover, during the period of measurement, no signs indicative of side effects (e.g., diarrhea, hypotensive action) were observed in any of the test groups.

Therefore, of the microspheres shown in Example 1 above, both the microspheres having a slow-release period of two weeks and the microspheres having a slow-release period of four weeks demonstrated the ability to continuously maintain a blood concentration sufficient for manifesting the pharmacological action of the present drug while avoiding side effects.

Example 3

SDF-1 and EGF Production Promoting Effects of the Present Drug

An angiogenesis kit (Kurabo Industries Ltd.) composed of normal human umbilical vein endothelial cells and normal human skin fibroblasts was procured and used.
Growth Method Using a carbon dioxide incubator (BNA-121D) and using Angiogenesis Culture 2 provided with the angiogenesis kit as the liquid culture, culturing was carried out in a wet environment at 37° C. with 5% carbon dioxide/95% air.
Test Procedure Immediately after the kit arrived, the cells were cultured for 3 hours, following which the liquid culture was replaced and culturing was continued. Three days after the start of culturing, the liquid culture was again replaced. Six days after the start of culturing, treatment with the present drug was carried out by replacing the liquid culture. The treatment concentration was set to 100 nmol/L in each case. DMSO treatment was carried out as a negative control. Six, 24, 48 and 72 hours after treatment with the present drug, the culture supernatant was collected and furnished for measurement of the growth factors. The measured growth factors were EGF and SDF-1.

The culture supernatant was measured with the following ELISA kits.
Human EGF Immunoassay (R&D Systems Inc., DEG00)
Human SDF-1α Immunoassay (R&D Systems Inc., DSA00)

The measurement results 72 hours after treatment with the present drug are shown below in Table 12.

TABLE 12

| Growth factor | Solvent control group (pg/mL) | Drug group (pg/mL) |
| --- | --- | --- |
| EGF | 3830 ± 423 | 4995 ± 442* |
| SDF-1 | 304 ± 24.2 | 383 ± 36.0* |

*$P < 0.05$ (Student's t-test)

The above results show that 72 hours after treatment with the present drug, the EGF and SDF-1 had significantly increased relative to the solvent control group.

Therefore, the present drug demonstrated an angiogenetic activity and a tissue regeneration promoting activity based on these growth factor production promoting effects.

Example 4

Investigation of Effects in a Common Carotid Artery Occlusion-Disobliteration (4-VO) Model 1) Preparation of Rat Common Carotid Artery Occlusion-Disobliteration (4-VO) Model Animals Nine-week-old male Crlj:WI rats were intraperitoneally administered pentobarbital sodium and, while under anesthesia, were secured in the prone position to a brain stereotaxic instrument. An occipital incision was made in the skin and muscle layer of the neck region, the left and right pterygoid foramina of the first cervical vertebra were exposed, and the vertebral arteries were thermocoagulated by inserting the tip of a soldering iron into each pterygoid foramen, thereby permanently occluding the bilateral vertebral arteries. Next, a midline incision was made in the anterior region of the neck, the common carotid arteries on both sides were exposed and detached, a silicone tube was passed under the arteries and placed annularly around the arteries, following which the skin of the neck region was sutured together. On the day after vertebral arterial cauterization, the animals were anesthetized with diethyl ether, then immobilized in the supine position. Both common carotid arteries were exposed using the silicone tube that had been placed on the common carotid arteries in the neck region and were temporarily occluded for 10 minutes with Sugita clips, then reopened. Aside from ischemia and disobliteration, the same procedure was carried out also on a normal group (Test Group 1).
2) Histopathological Study Following four-point ischemia and disobliteration of the rats, a specific dosing period of 8 days or 42 days+a drug-free period (of at least 2 weeks) was provided. The animals were then pentobarbital sodium anesthetized, perfused and fixed with, in order, physiological saline, 4% paraformaldehyde and Bouin's solution, and the brains removed. Tissue near the bregma—3.3 mm was excised from the Bouin's solution-fixed brain. Following dehydration and dewaxing, the specimen was embedded in paraffin. Four sections of 10 μm thickness were prepared from the bregma—approx. 3.3 mm site. The number of CA1 nerve cells in one of the sections was measured using Nissl's stain. Another of the sections was PCNA stained (microglia), and a third section was GFAP stained (glia).
Test 1. Study on Subcutaneous Administration of Prostaglandins The effects of the repeated subcutaneous administration of ornoprostil, $PGE_1 \cdot \alpha CD$ and the present drug, twice daily for 42 days following creation of the rat 4-VO model (10 minutes of occlusion and reperfusion), on the number of nerve cells in the CA1 region of the hippocampus was investigated.

The groups consisting of a normal group (Test Group 1, evaluated after receiving medium for 42 days), control groups (Test Group 2, evaluated after receiving solvent for 8 days; Test Group 3, evaluated after receiving medium for 42 days), present drug (Test Group 4, repeatedly given subcutaneously 10 mg/kg twice daily for 42 days), ornoprostil (Test Group 5, repeatedly given subcutaneously 0.1 mg/kg twice daily for 42 days), and prostaglandin E1 (PGE$_1$•αCD) groups (Test Group 6, repeatedly given subcutaneously 1.5 mg/kg twice daily for 42 days; Test Group 7, repeatedly given subcutaneously 3 mg/kg twice daily for 42 days). The dose of PGE1•αCD is the dose as PGE1. The present drug and ornoprostil were each set to the maximum dose at which a hypotensive action is not exhibited.

Evaluation: After 8 days in Test Group 2, and after 42 days in the other test groups, the brains were perfused and fixed, then Nissl stained, H-E stained or GFAP stained, and the number of nerve cells in the hippocampal CA1 region counted. (The number of nerve cells at 10 places in each of the CA1a, CA1b and CA1c regions, and at 20 places on the left and right sides were counted by photographing each place and counting the number of mature nerve cells with an image analyzer (Win ROOF V3.6; Mitani Corporation)).

The results obtained with Nissl staining are shown below in Table 13.

TABLE 13

| Test group | Number of nerve cells per unit length (count/mm) | |
|---|---|---|
| | Left (L) | Right (R) |
| 1 | 92.2 ± 19.1 | 96.4 ± 16.9 |
| 2 | 43.2## ± 12.8 | 33.0## ± 13.2 |
| 3 | 58.7## ± 20.4 | 54.7## ± 29.5 |
| 4 | 134.4** ± 25.7 | 123.8** ± 30.9 |
| 5 | 134.6** ± 32.7 | 141.1** ± 17.8 |
| 6 | 105.7 ± 24.0 | 114.7** ± 22.0 |
| 7 | 146.2** ± 39.6 | 127.6** ± 38.8 |

P < 0.01 vs. Test Group 1 (Dunnett's test)
*, **P < 0.05, P < 0.01 vs. Test Group 3 (Dunnett's test)

The medium, the present drug, PGE$_1$•αCD and ornoprostil were subcutaneously administered once immediately after 4-VO ischemia and reperfusion, and twice daily from day 1 to day 8 of ischemia or from day 1 to day 42 of ischemia. After 8 days or 42 days, the brain was perfused and fixed, following which the numbers of pyramidal nerve cells in the left and right hippocampal CA1 region were measured by means of Nissl staining.

As a result, relative to the normal group (Test Group 1), in ischemia and disobliteration (4-VO), hippocampal CA1 region nerve cells showed a significant decrease on day 8 (Test Group 2) and the number of cells did not increase even after 42 days (Test Group 3). By contrast, on day 42 of ischemia, the subcutaneous administration of the present drug, ornoprostil, and PGE$_1$•αCD (both 1.5 mg/kg and 3 mg/kg) all showed a significant increase in the number of hippocampal CA1 pyramidal nerve cells relative to the group given the medium (Test Group 3). Administration of each of the test substances was confirmed to have a neuronopathy preventing action and/or a nerve cell regeneration promoting action.

Test 2. Study of Repeated Oral Administration of Present Drug

The nerve cell regeneration promoting action by the twice daily repeated oral administration of the present drug following a disorder was confirmed, and the effects of such administration on water maze learning impairment was investigated.

Groups: Each group consisting of n=12 animals
(1) Evaluation of number of nerve cells in hippocampal CA1 region excised from brain
  Test Group 1: 4-VO+medium, 8 days
  Test Group 2: 4-VO+present drug, 10 mg/kg, twice daily, for 8 days
  Test Group 3: 4-VO+present drug, 1 mg/kg, twice daily, for 42 days (evaluation of nerve cell number only)
(2) Evaluation of number of nerve cells in CA1 region excised from brain (Groups 4 to 7) following measurement of water maze learning ability (Groups 4 to 7)
  Test Group 4: normal (sham group)+medium, 42 days (normal control)
  Test Group 5: 4-VO+medium, 42 days (solvent control)
  Test Group 6: 4-VO+present drug, 10 mg/kg, twice daily for 42 days
  Test Group 7: 4-VO+solvent for 8 days+present drug, 10 mg/kg, twice daily, for 34 days (evaluation of regenerative activity)
(3) Pathology: Perfusion and fixing of the brain was carried out on day 8 in Test Groups 1 and 2, and on the day after the water maze learning ability test in Groups 4 to 7. The number of nerve cells was then counted by the same method as described above in Test 1. In Test Group 3, after drug administration was stopped, the brains were fixed at the same time as in Test Groups 4 to 7.
(4) Measurement of Water Maze Learning Ability Using Test Groups 3 to 7, the motor functions were investigated with a Morris water maze in such a way as to avoid a bias between the groups.

Apparatus for Testing Water Maze Learning Ability

A clear acrylic platform (about 12 cm in diameter and about 30 cm in height) which cannot be visually detected and a circular pool (about 148 cm in diameter and about 44 cm in height) made of gray vinyl chloride and filled with water (water temperature, 17 to 18° C.) to a height of about 32 cm so that the platform is hidden by the water were used.

The pool was divided into four quadrants, the platform was placed at the center of the fourth quadrant (about 36 cm from the center of the pool), and light bulbs were placed at the perimeter of the pool to provide a spatial reference.

Measurement of Water Maze Learning Acquisition Trials

Following the final drug dose, a drug-free period of at least 2 weeks was provided, after which the rat was placed in the pool from one of several points A to E with its head facing the circular pool wall, and the time it took to reach the platform (goal latency; seconds) was measured with a stopwatch (the measurement time was a maximum of 90 seconds). When the rat reached the platform within 90 seconds and remained on the platform for 30 seconds, it was judged to be aware of the platform location and measurement was brought to an end. Rats that did not reach the platform were assigned a goal latency of 90 seconds.

Goal latency measurements were carried out twice daily (once in the morning, and once in the afternoon) on days 1 to 4. The rat was placed in the pool from the various points A to E with its head facing the wall of the circular pool. The swimming path of the rat was captured on a TV monitor with a video camera installed over the pool, and the swimming time, distance traveled and number of passes were analyzed with a video image movement analyzer (SMART, Panlab). In addition, the swimming movements were recorded using a DVD video recorder. The results are presented in Tables 14 to 17 below.

1) Number of nerve cells in hippocampal CA1 region of Test Groups 1 and 2

TABLE 14

| Test group | Number of nerve cells per unit length (count/mm) | |
|---|---|---|
| | Left (L) | Right (R) |
| 1 | 11.03 ± 6.01 | 20.05 ± 39.00 |
| 2 | 90.97** ± 53.70 | 89.70** ± 51.89 |

**$P < 0.01$ vs. Test Group 1 (Dunnett's test)

As is apparent from the above results, oral administration following ischemia and reperfusion in Test Group 2 already exhibited on day 8 a significant suppression in the decrease in the number of hippocampal CA1 region nerve cells relative to Test Group 1, thus confirming the existence of a neuronopathy preventing activity.

2) Number of Nerve Cells in Hippocampal CA1 Region of Test Groups 3 to 7

TABLE 15

| Test group | Number of nerve cells per unit length (count/mm) | |
|---|---|---|
| | Left (L) | Right (R) |
| 4 | 163.13 ± 14.21 | 162.39 ± 10.13 |
| 5 | 24.08** ± 24.89 | 19.69** ± 22.45 |
| 3 | 73.65# ± 49.14 | 63.09# ± 43.97 |
| 6 | 91.22$^{aa}$ ± 49.48 | 76.44$^{aa}$ ± 47.56 |
| 7 | 48.35$^+$ ± 34.39 | 43.29$^+$ ± 32.93 |

**$P < 0.01$ vs. Test Group 4 (Aspin-Welch's t-test or Student's t-test)
$P < 0.05$ vs. Test Group 5 (Aspin-Welch's t-test)
$^{aa}P < 0.01$ vs. Test Group 5 (Dunnett's test)
$^+P < 0.1$ vs. Test Group 5 (Student's t-test)

The group given the medium (Test Group 5, after 42 days in 4-VO model) exhibited a significant decrease in the number of hippocampal CA1 nerve cells relative to the normal group (Test Group 4). By contrast, the oral administration of the present drug at a level of 1 mg/kg (Test Group 3) and a level of 10 mg/kg (Test Group 6) showed significant increases in the number of hippocampal CA1 region nerve cells relative to Test Group 4. Moreover, it is known that, in this evaluation system, nerve cell death in the hippocampal CA1 region is complete after about 5 days of ischemia and disobliteration. Even when medium was administered up to day 8 and 10 mg/kg of the present drug was repeatedly administered orally for 34 days starting on day 9 (Test Group 7), an increasing trend in the number of hippocampal CA1 region nerve cells was observed. Hence, in addition to a nerve cell protecting activity, the present drug was confirmed to have a nerve cell regeneration promoting activity.

3) Measurement of Water Maze Learning Ability (1) Time Until the Rat Reaches the Platform (Goal Latency, Seconds)

TABLE 16

| Test group | Number of animals | Goal latency (seconds) Acquisition trials | | | | | AUC for Trials 1 to 8 | AUC for Days 1 to 4 (average) |
|---|---|---|---|---|---|---|---|---|
| | | Day 1 (average) | Day 2 (average) | Day 3 (average) | Day 4 (average) | Trials 1 to 8 (average) | | |
| 4 | 12 | 66.9 ± 16.0 | 47.7 ± 27.5 | 28.0 ± 20.9 | 27.6 ± 24.1 | 42.5 ± 12.3 | 289.5 ± 88.9 | 122.9 ± 38.3 |
| 5 | 16 | 76.6 ± 20.7 | 65.9 ± 21.1 | 53.8 ± 24.0 | 37.6 ± 22.3 | 58.5 ± 16.2 | 405.7### ± 115.7 | 176.8 ± 50.5 |
| 6 | 12 | 71.8 ± 18.3 | 58.8 ± 22.1 | 41.3 ± 28.8 | 33.9 ± 23.2 | 51.5 ± 11.9 | 358.3* ± 89.9 | 152.9 ± 42.7 |
| 7 | 12 | 73.8 ± 15.2 | 55.4 ± 29.6 | 41.7 ± 26.7 | 25.8 ± 15.2 | 49.2 ± 10.1 | 338.4** ± 80.8 | 146.9 ± 40.5 |

The values in the table indicate the mean ± standard deviation.
: $P < 0.01$ vs. Group 4
*, **: $P < 0.1$, $P < 0.05$ vs. Group 5 (two-way analysis of variance (8 trials))

(2) Distance Traveled Until Rat Reaches Platform

TABLE 17

| Test group | Number of animals | Goal latency (seconds) Acquisition trials | | | | | AUC for Trials 1 to 8 | AUC for Days 1 to 4 (average) |
|---|---|---|---|---|---|---|---|---|
| | | Day 1 (average) | Day 2 (average) | Day 3 (average) | Day 4 (average) | Trials 1 to 8 (average) | | |
| 4 | 12 | 1458.1 ± 417.6 | 1250.5 ± 573.5 | 846.2 ± 654.6 | 720.9 ± 463.7 | 1068.9 ± 280.0 | 7498.1 ± 2087.8 | 3186.2 ± 945.0 |
| 5 | 16 | 1684.7 ± 474.3 | 1733.2 ± 518.1 | 1476.4 ± 583.8 | 1108.8 ± 572.3 | 1500.8 ± 378.4 | 10534.0### ± 2710.8 | 4606.4 ± 1174.6 |
| 6 | 12 | 1513.2 ± 414.1 | 1531.8 ± 558.8 | 1176.1 ± 773.4 | 936.6 ± 525.6 | 1289.4 ± 296.7 | 9190.9** ± 2281.9 | 3932.8 ± 1115.1 |
| 7 | 12 | 1571.5 ± 356.1 | 1492.1 ± 743.7 | 1164.3 ± 603.5 | 816.7 ± 409.4 | 1261.2 ± 214.7 | 8901.5** ± 1807.4 | 3850.5 ± 832.5 |

The values in the table indicate the mean ± standard deviation.
: $P < 0.01$ vs. Group 4
**: $P < 0.05$ vs. Group 5 (two-way analysis of variance (8 trials))

The solvent control group (Test Group 5) showed a significant extension in the goal latency (seconds) and distance traveled relative to the normal group (Test Group 4) in the water maze learning ability trials. The group that was orally given 10 mg/kg, twice daily, of the present drug (Test Group 6) and the group that was given the medium up to day 8 and orally given 10 mg/kg, twice daily, of the present drug starting on day 9 (Test Group 7) both showed a significant shortening in goal latency (seconds) and distance traveled in the water maze learning ability trials relative to the solvent control group (Test Group 5) (test: two-way analysis of variance; 8 trials).

Therefore, the present drug, by exhibiting a nerve protecting activity and an endogenous nerve cell regeneration promoting activity, was confirmed to not only increase the number of nerve cells, but also to aid in the recovery of learning function disabilities associated with neuropathy.

Test 3. Study of Single Subcutaneous Administration of Microspheres of the Present Invention; Study of Nerve Cell Regeneration Promoting Activity and Effects on Behavioral Pharmacology (1) Influence on Number of Nerve Cells in Hippocampal CA1 Region This study was performed in the same way as in Test 1, and the results were evaluated based on the number of hippocampal CA1 nerve cells.

In a rat 4-VO model, following 10 minutes of occlusion and reperfusion, the microspheres produced in Preparation Example 2-2 were subcutaneously administered one time only, and the influence on the number of nerve cells in the hippocampal CA1 region 42 days later was evaluated. The dose indicates the amount of the present drug included in the microspheres. The PLGA•MS doses in Test Groups 1 and 2 were the same as in Test Groups 3, 5, 6 and 7.

The groups are shown in Table 18 below.

TABLE 18

| Test group | Substance administered | Dose/Method of administration | Number of animals |
|---|---|---|---|
| 1 | Normal (medium) | 0 mg/kg (single subcutaneous administration) | 10 |
| 2 | Solvent control | 0 mg/kg (single subcutaneous administration) | 11 |
| 3 | Microspheres produced in Preparation Example 2-2 | 10 mg/kg (single subcutaneous administration just after ischemia and reperfusion) | 14 |
| 4 | Microspheres produced in Preparation Example 2-2 | 30 mg/kg (single subcutaneous administration just after ischemia and reperfusion) | 11 |
| 5 | Microspheres produced in Preparation Example 2-2 | 10 mg/kg (single subcutaneous administration 48 hours after ischemia and reperfusion) | 11 |
| 6 | Microspheres produced in Preparation Example 2-2 | 10 mg/kg (single subcutaneous administration 7 days after ischemia and reperfusion) | 9 |
| 7 | Microspheres produced in Preparation Example 2-2 (for measuring blood kinetics) | 10 mg/kg (single subcutaneous administration just after ischemia and reperfusion) | 6 |

Test Group 1: Normal group (sham group); normal rats on which sham surgery was performed were given a single subcutaneous administration of PLGA•MS alone as a negative control.

Test Group 2: Solvent control group; 4-VO rats were given a single subcutaneous administration of PLGA•MS alone as a negative control.

Test Group 3: The microspheres produced in Preparation Example 2-2 were subcutaneously administered once (10 mg/kg) just after 4-VO ischemia and reperfusion.

Test Group 4: The microspheres produced in Preparation Example 2-2 were subcutaneously administered once (30 mg/kg) just after 4-VO ischemia and reperfusion.

Test Group 5: The microspheres produced in Preparation Example 2-2 were subcutaneously administered once (10 mg/kg) 48 hours after 4-VO ischemia and reperfusion.

Test Group 6: The microspheres produced in Preparation Example 2-2 were subcutaneously administered once (10 mg/kg) 7 days after 4-VO ischemia and reperfusion.

Test Group 7: (Blood concentration measurement use) The microspheres produced in Preparation Example 2-2 were subcutaneously administered once (10 mg/kg) just after 4-VO ischemia and reperfusion (as in Test Group 3).

After 42 days, the rat brains were perfused and fixed, following which the pyramidal nerve cells of the left and right hippocampal CA1 regions were Nissl-stained and the numbers of nerve cells in the hippocampal CA1 regions were determined (the number of nerve cells at 10 places in each of regions CA1a, CA1b and CA1c, and at 20 places on the left and right sides were counted using an image analyzer). The results are shown in Table 19.

As a result, the control group (Test Group 2) showed a significant decrease in the number of hippocampal CA1 pyramidal nerve cells relative to the normal group (Test Group 1), and the groups subcutaneously administered the microspheres of the invention (Test Groups 3 to 6) were all found to have a significantly increased number of hippocampal CA1 pyramidal nerve cells relative to the control group (Test Group 2).

TABLE 19

| | Number of nerve cells per unit length (count/mm) | |
|---|---|---|
| Test group | Left (L) | Right (R) |
| 1 | 175.3 ± 14.0 | 179.7 ± 11.8 |
| 2 | 9.1## ± 3.2 | 9.1## ± 2.9 |
| 3 | 25.6** ± 14.0 | 28.7** ± 15.9 |
| 4 | 34.1** ± 16.7 | 31.1** ± 24.5 |
| 5 | 47.2++ ± 33.2 | 48.9++ ± 38.3 |
| 6 | 47.7+ ± 41.6 | 51.7+ ± 41.7 |

The values in the table indicate the mean ± standard deviation.
$p < 0.01$ vs. Group 1 (Aspin-Welch's t-test)
*, **$p < 0.05, p < 0.01$ vs. Group 2 (Dunnett's test)
+, ++$p < 0.05, p < 0.01$ vs. Group 2 (Aspin-Welch's t-test)

From the above results, a single subcutaneous administration of the microspheres of the invention (Test Groups 3 to 6) was confirmed to have an excellent neuronopathy preventing activity and/or nerve cell regeneration promoting activity. Also, even with a single subcutaneous administration after 7 days in Group 6, the number of nerve cells rose significantly relative to Group 2, demonstrating the presence of a nerve cell regeneration promoting action.

2) Passive Avoidance Response Test

A step-through type passive avoidance response apparatus (SHOCK SCRAMBLER, Takei Scientific Instruments Co., Ltd.) was used. The apparatus had, partitioned by a center guillotine door, a light room (260 (W)×110 (D)×290 (H)) and a dark room (320 (W)×320 (D)×340 (H)) which imparts an electrical stimulus from a floor grid. A rat was placed in the light room, the guillotine door was quietly opened, and the time that elapsed from when the rat examined the opening until it entered the dark room (response latency) was measured. As soon as the rat entered the dark room, the guillotine door was closed and an electric stimulus (1 mA, 3 sec, scramble method) was applied. This constituted an acquisition trial. The acquisition trial was carried out two days before removal of the brain. A retention trial was carried out one day after the learning trial. As in the acquisition trial, the rat was placed in a light room, the guillotine door was quietly opened, and the time that elapsed from when the rat examined the opening until it entered the dark room (response latency) was measured. The response latency of the retention trial was set to a maximum of 600 seconds. The results are shown below in Table 20.

TABLE 20

| Test group | Response latency (sec) | | Number of animals |
|---|---|---|---|
| | Acquisition trial | Retention trial | |
| 1 | 66.7 ± 63.1 | 600.0 ± 0.0 | 10 |
| 2 | 30.6 ± 12.1 | 305.0# ± 284.0 | 11 |
| 3 | 39.3 ± 19.4 | 432.8 ± 274.3 | 14 |
| 4 | 33.8 ± 22.3 | 345.7 ± 280.3 | 11 |
| 5 | 57.0 ± 68.6 | 600.0* ± 0.0 | 11 |
| 6 | 36.8 ± 31.6 | 434.6 ± 260.5 | 9 |

The values in the table indicate the mean ± standard deviation.
$p < 0.05$ vs. Group 1 (Wilcoxon's test)
*$p < 0.05$ vs. Group 2 (Wilcoxon's test)

Test Group 2 had, relative to Test Group 1, a shortened retention trial response latency, indicating that a memory/learning disability had arisen. On the other hand, Test Groups 3 to 6 showed, relative to Test Group 2, an extended retention trial response latency. In particular, Test Group 5 showed a significant extension in the response latency.

Therefore, the microspheres of the present invention demonstrated a neuronopathy preventing activity and/or a nerve cell regeneration promoting activity, and were thus confirmed to aid in functional recovery from neuropathy.

From the above results, relative to the repeated subcutaneous administration of the present drug (Test 1.) and the repeated oral administration of the present drug (Test 2.), a single subcutaneous administration of the microspheres of the invention (Test Groups 3 to 6) was found to have, in terms of efficacy, safety, cumulative dosage of the present drug and dose compliance, excellent neuronopathy-preventing and nerve cell regeneration-promoting activities, and functional recovery from memory and learning disorders was confirmed.

3) Measurement of Blood Concentration

Figure 3:
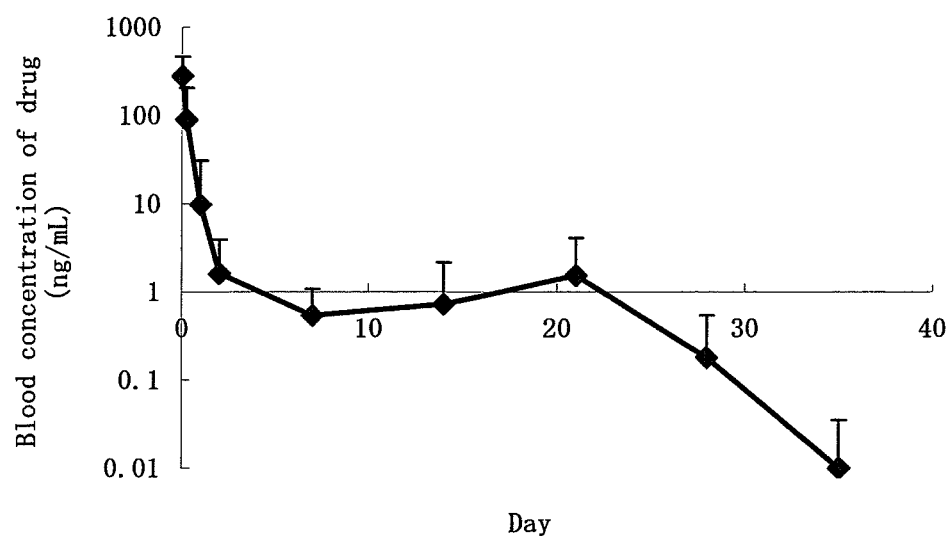
FIG. 3 shows, in a rat 4-VO model, the blood kinetics of the present drug when the microspheres produced in Preparation Example 2-2 were administered a single time (10 mg/kg) subcutaneously.

Using Test Group 7 specimens, FIG. 3 shows results illustrating the blood kinetics of the present drug. The procedure was the same as that used in Example 2.

It was confirmed from the above that, in 4-VO rats, the blood concentration of the present drug is continuously maintained in a range of from 0.1 to 10 ng/mL for a period of four weeks starting 24 hours after a single subcutaneous administration of the microspheres of the present invention.

The above suggests that the microspheres of the invention, because they have a nerve cell regeneration promoting activity, are useful for preventing and/or treating nerve degeneration diseases, and particularly strokes.

Example 5

Influence on Nerve Conduction Velocity in STZ Induced Diabetes Model

1) Preparation of STZ Induced Diabetes Model Animals

Female Sprague-Dawley rats (8- to 11-week-old; Japan SLC, Inc.) were intraperitoneally administered 40 mg/kg of a citrate buffer (pH, approx. 4.5) of streptozotocin (STZ; Sigma). A normal control group was intraperitoneally given only the citrate buffer.

2) Measurement of Blood Sugar

Two weeks after STZ administration, the blood sugar, nerve conduction velocity and body weight were measured, the animals were divided into groups uniform for these properties, and administration of the test substance was begun. To determine the change over time in blood sugar, the blood sugar level was measured 4, 8 and 12 weeks following the start of test solution administration (on the day prior to nerve conduction velocity measurement). The blood sugar level of blood drawn from the caudal vein was measured using a blood sugar analyzer (Antisense II; Bayer-Sankyo). Following measurement of the blood sugar 12 weeks later, the animals were deprived of food for at least 16 hours and the fasting blood sugar and insulin were measured. In addition, a 2 g glucose tolerance test was carried out in which blood was similarly drawn 30, 60 and 120 minutes after sugar loading, and the blood sugar and insulin values were measured.

3) Measurement of Nerve Conduction Velocity

Two weeks after STZ administration, and 4, 8 and 12 weeks after the start of test solution administration, the animals were anesthetized by the intraperitoneal administration of 30 to 45 mg/kg of pentobarbital. Fur was removed from the dorsolumbar region of the rat and the animal was immobilized in the prone position, following which a needle electrode for distal stimulation (NEC Medical Systems) was inserted near the sciatic nerve, a needle electrode for proximal stimulation was inserted near the Achilles tendon on the same side, and a recording needle electrode (NEC Medical Systems) was inserted in the plantar muscle on the same side. After checking that the body temperature was in a range of 37 to 38° C., square-wave stimulation (0.5 Hz, 0.1 msec, submax voltage) to the distal and proximal stimulating electrodes was applied using an electrical stimulator (SEN-3301; Nihon Kohden Corporation). The evoked potential was led out via a measuring electrode, input through a bioelectric amplifier (AB-621G, Nihon Kohden Corporation) to an evoked electromyogram averaging program (MTS50061C, Medical Try System) and averaged ten times, and the nerve conduction velocity was computed from the respective distal and proximal conduction times and the electrode interval distances. Measurement was carried out on the left leg (treated side) and right leg (untreated side) in each test group, and the respective average values thereof used as the data.

4) Grouping Method

In Groups 2 to 5, the feeding blood sugar level two weeks after STZ administration was measured. Of rats with blood sugar levels above 300 mg/dL, severely diabetic rats were excluded therefrom, and the remaining rats were used as diabetes model animals. Groups were formed in such a way as to make the respective groups uniform with respect to nerve conduction velocity, blood sugar level and body weight.

5) Method of Administration

Administration was carried out in accordance with the intended route of administration for clinical use. In Test Group 3, forced administration was carried out orally using a disposable syringe barrel and a rat stomach probe. In Test Group 4, intramuscular administration was carried out uniformly at four places within the muscle along the sciatic nerve in the femoral portion of the left leg. For subcutaneous administration in test Group 5, the animals were ether anesthetized, and subcutaneous administration was carried out in the dorsal region using a disposable syringe barrel and a disposable 25 G syringe needle. The volume of solution administered was computed based on the latest body weight.

6) Groups

The composition of the groups is shown below in Table 21.

TABLE 21

| Test group | Substance administered | Dose/Method of administration | Number of animals |
|---|---|---|---|
| 1 | normal (medium) | 0 mg/kg (intermittent intramuscular administration given once every 3 weeks) | 10 |
| 2 | Solvent control | 0 mg/kg (intermittent intramuscular administration given once every 3 weeks) | 10 |
| 3 | present drug | 3 mg/kg (twice daily repeated oral administration) | 10 |
| 4 | Microspheres produced in Preparation Example 2-2 | 10 mg/kg (intermittent intramuscular administration given once every 3 weeks) | 10 |
| 5 | Microspheres produced in Preparation Example 2-2 | 10 mg/kg (intermittent subcutaneous administration given once every 3 weeks) | 10 |

The amount of microspheres administered indicates the amount of the present drug included. The amount of microspheres that do not contain the present drug in Test Group 2 was the same as the amount of microspheres given the animals in Test Groups 4 and 5.

7) Time Course of Blood Sugar Level

The change over time in the blood sugar level in each test group is shown below in Table 22.

TABLE 22

| Test group | Blood sugar (mg/dL) | | | |
|---|---|---|---|---|
| | 0 weeks | 4 weeks | 8 weeks | 12 weeks |
| 1 | 116 ± 11 | 118 ± 8 | 122 ± 6 | 108 ± 11 |
| 2 | 578## ± 72 | 590## ± 47 | 651## ± 72 | 566# ± 81 |
| 3 | 567 ± 73 | 555 ± 39 | 600 ± 64 | 510 ± 84 |
| 4 | 560 ± 60 | 541* ± 30 | 561* ± 79 | 479** ± 40 |
| 5 | 576 ± 71 | 561 ± 66 | 541** ± 69 | 474** ± 41 |

The values in the table indicate the mean ± standard deviation.
, ##p < 0.05, p < 0.01 vs. Group 1 (Welch's t-test)
*, **p < 0.05, p < 0.01 vs. Group 2 (Student's t-test)

From the results in Table 22, Test Group 4 showed a significant decline in blood sugar after four weeks relative to Test Group 2. Similarly, Test Groups 4 and 5 showed significant declines in blood sugar after 8 weeks and 12 weeks relative to Test Group 2. A significant decline in blood sugar was not observed at any of the times in Test Group 3.

8) Left (Drug-Treated Side) Nerve Conduction Velocity

Table 23 below shows the time course for nerve conduction velocity in the left leg (drug-treated side in four groups) in the respective test groups.

TABLE 23

| Test group | Nerve conduction velocity (m/sec) | | | |
|---|---|---|---|---|
| | 0 weeks | 4 weeks | 8 weeks | 12 weeks |
| 1 | 42.3 ± 5.3 | 42.4 ± 3.9 | 42.6 ± 3.7 | 49.3 ± 2.9 |
| 2 | 37.8 ± 5.1 | 38.7# ± 3.2 | 38.6## ± 3.0 | 41.2# ± 1.8 |
| 3 | 37.5 ± 8.0 | 37.8 ± 3.8 | 40.8 ± 3.4 | 43.1* ± 1.9 |
| 4 | 37.1 ± 5.4 | 39.8 ± 3.6 | 43.4** ± 3.6 | 46.2** ± 2.2 |
| 5 | 35.3 ± 4.5 | 37.9 ± 2.7 | 41.7* ± 2.7 | 44.2** ± 2.1 |

The values in the table indicate the mean ± standard deviation.
, ##p < 0.05, p < 0.01 vs. Group 1 (Student's t-test)
*, **p < 0.05, p < 0.01 vs. Group 2 (Student's t-test)

From the results in Table 23, Test Group 2 showed a significant decline in nerve conduction velocity after 4 weeks, 8 weeks and 12 weeks relative to Test Group 1, confirming the onset of diabetic neuropathy. By contrast, Test Groups 4 and 5 showed significant increases in the nerve conduction velocity after 8 weeks relative to Test Group 2, and Test Groups 3, 4 and 5 showed significant nerve conduction velocity increases after 12 weeks relative to Test Group 2, although the latter effect was better in Test Groups 4 and 5 than in Test Group 3. These results demonstrate the usefulness of the drug blood concentration sustaining effect. After 8 weeks and 12 weeks, the nerve conductive velocity increasing effect in Test Group 4 was better than that in Test Group 5, confirming that local administration at the site of disease is more useful than systemic administration.

9) Right (Drug-Untreated Side) Nerve Conduction Velocity

Table 24 below shows the time course for nerve conduction velocity in the right leg (drug-untreated side) in the respective test groups.

TABLE 24

| Test group | Nerve conduction velocity (m/sec) | | | |
|---|---|---|---|---|
| | 0 weeks | 4 weeks | 8 weeks | 12 weeks |
| 1 | 43.2 ± 4.6 | 46.5 ± 7.8 | 42.9 ± 2.9 | 48.0 ± 2.9 |
| 2 | 38.2# ± 4.5 | 39.4# ± 3.0 | 37.7## ± 3.0 | 40.5# ± 3.1 |
| 3 | 38.7 ± 5.0 | 39.0 ± 2.3 | 39.9 ± 2.2 | 41.3 ± 2.1 |
| 4 | 38.6 ± 6.3 | 39.4 ± 3.7 | 40.8* ± 3.1 | 41.7 ± 3.2 |
| 5 | 36.5 ± 3.8 | 39.3 ± 4.3 | 41.0* ± 3.1 | 43.8* ± 1.9 |

The values in the table indicate the mean ± standard deviation.
, ##p < 0.05, p < 0.01 vs. Group 1 (Student's t-test)
*p < 0.05 vs. Group 2 (Student's t-test)

From the results in Table 24, Test Group 2 showed a significant decline in nerve conduction velocity after 0 weeks, 4 weeks, 8 weeks and 12 weeks relative to Test Group 1, confirming the onset of diabetic neuropathy. By contrast, Test Groups 4 and 5 showed significant nerve conduction velocity increasing trends after 8 weeks and 12 weeks relative to Test Group 2, with the effects being substantially the same in both (Groups 4 and 5). A significant extension effect was not confirmed at any of the times in Test Group 3.

From these results, intermittent administration of the microspheres of the invention provided continuous blood kinetics relative to the twice daily repeated oral administration in Test Group 3, and was thus confirmed to be useful in terms of efficacy, safety, total dosage and dose compliance. Also, in the intermittent administration of the microspheres of the invention, because intramuscular injection to the site of disease (Test Group 4) was more effective than systemic administration subcutaneously in the dorsal region (Test Group 5), the usefulness of maintaining a high concentration of the present drug at the site of disease was confirmed.

10) Nephropathy Ameliorating Action

In week 12 from the start of test substance administration, the rats were transferred to a metabolic cage, given water ad libitum, and the urine was collected for 24 hours. Following measurement of the urinary discharge, the urine was centrifuged (1500 rpm, 25° C., 10 minutes) with a centrifuge, and the supernatant was collected. Using the 7170 Clinical Analyzer (Hitachi, Ltd.), the total urinary protein (pyrogallol red method), creatinine (creatinase/F-DAOS method) and urine sugar were measured. Table 25 below shows the total urinary discharge, total urinary creatinine, total protein and glucose excretion calculated from the measured results (concentrations).

TABLE 25

| Total group | Total excretion (mg/24 hrs) | | |
|---|---|---|---|
| | Glucose | Creatinine | Total protein |
| 1 | 32 ± 28 | 80.31 ± 57.65 | 26.5 ± 26.7 |
| 2 | 139397## ± 86550 | 147.05## ± 137.74 | 216.9# ± 370.6 |
| 3 | 111174 ± 40497 | 116.76 ± 58.15 | 245.7 ± 231.9 |
| 4 | 114850 ± 54081 | 99.26 ± 49.91 | 104.0 ± 40.7 |
| 5 | 124280 ± 50604 | 156.92 ± 135.34 | 169.6 ± 150.2 |

The values in the table indicate the mean ± standard deviation.
, ##p < 0.05, p < 0.01 vs. Group 1 (Aspin-Welch's t-test)

From the results in Table 25, the urinary glucose, creatinine and total protein increased in Test Group 2 relative to Test Group 1, indicating the onset of diabetic nephropathy. On the other hand, in Test Groups 4 and 5, decreasing trends in total urinary creatinine, sugar and total protein excretion relative to Test Group 2 were observed, indicating an improving trend in renal function.

11) Oral Glucose Tolerance Test (OGTT)

Thirteen weeks after the start of test substance administration, an oral glucose tolerance test (OGTT) was conducted on rats fasted for 18 hours. After drawing blood from the caudal vein of the fasting rats, 2 g/kg of glucose was orally force-fed. About 500 µL of blood was similarly collected from the caudal vein 30, 60 and 120 minutes after glucose administration, of which about 400 µL was EDTA-2Na treated, then centrifuged (3,000 rpm, 4° C., 10 min) with a centrifuge. The plasma was thereby collected, and the blood sugar was measured using a 7170 Clinical Analyzer (Hitachi, Ltd.). The remaining approximately 100 µL of blood was centrifuged (3,000 rpm, 4° C., 10 min) with a centrifuge, the serum was collected, and the insulin level was measured (ELISA method; Levis Insulin Kit (Shibayagi Co., Ltd)). Table 26 below shows the insulin measurement results.

TABLE 26

| Test group | Insulin (ng/mL) | | | |
|---|---|---|---|---|
| | Before glucose loading | After 30 minutes | After 60 minutes | After 120 minutes |
| 1 | 1.418 ± 0.908 | 4.289 ± 2.035 | 3.167 ± 2.035 | 2.072 ± 1.415 |
| 2 | 0.946 ± 0.732 | 0.989## ± 0.804 | 0.909## ± 0.851 | 0.935## ± 0.764 |
| 3 | 2.138 ± 1.722 | 2.197 ± 2.062 | 1.808 ± 1.521 | 2.130 ± 2.087 |
| 4 | 2.341+ ± 1.907 | 2.275+ ± 1.902 | 2.125+ ± 1.862 | 2.342+ ± 2.093 |
| 5 | 1.706 ± 0.556 | 1.616 ± 1.440 | 1.445 ± 1.496 | 1.370 ± 1.086 |

The values in the table indicate the mean ± standard deviation.
p < 0.01 vs. Group 1 (Student's t-test)
+p < 0.1 vs. Group 2 (Student's t-test)

From the results in Table 26, Test Group 2 showed a significant decline in the level of insulin relative to Test Group 1. On the other hand, Test Group 4 showed a significant increasing trend in the level of insulin relative to Test Group 2, confirming a insulin synthesis and secretion promoting effect.

12) Influence on Body Weight

The rat body weights were measured before test substance administration and 14 weeks after the start of test substance administration. The results are shown below in Table 27.

TABLE 27

| Test group | Body weight (g) | |
|---|---|---|
| | 0 weeks | 14 weeks |
| 1 | 238.2 ± 15.3 | 307.3 ± 19.7 |
| 2 | 231.2 ± 14.2 | 252.1## ± 24.9 |

TABLE 27-continued

| Test group | Body weight (g) | |
|---|---|---|
| | 0 weeks | 14 weeks |
| 3 | 219.1 ± 12.2 | 224.7* ± 27.8 |
| 4 | 229.7 ± 9.2 | 243.5 ± 25.3 |
| 5 | 230.4 ± 11.5 | 252.8 ± 27.7 |

The values in the table indicate the mean ± standard deviation.
p < 0.01 vs. Group 1 (Student's t-test)
*p < 0.05 vs. Group 2 (Student's t-test)

From the results in Table 27, at week 14 following the start of administration, the body weight in Test Group 2 showed a significant decreased relative to Test Group 1. On the other hand, Test Group 3 shows a significant weight decreased relative to Test Group 2, but because Test Groups 4 and 5 were about the same as Test Group 2, the microspheres of the invention were confirmed to have no influence on body weight.

The above results demonstrate that the microspheres of the present invention have no influence on body weight and, in intermittent intramuscular administration and subcutaneous administration in the dorsal region once every three weeks, exhibit decrease of the blood sugar level during feeding and elevating effect of an insulin biosynthesis/secretion, due to a pancreatic β cell regeneration promoting action, during glucose loading. Also, in the intramuscular injection and subcutaneous administration of the microspheres of the present invention, a significant nerve conduction velocity-improving action was observed. Intramusuclar administration to the site of disease was found to be more effective, and was confirmed to be effective against diabetic neuropathy. Also, the microspheres of the present invention were shown to be effective against diabetic nephropathy by lowering urinary creatinine and total protein excretion. The declines in blood sugar levels observed in these results were effects of a degree that do not exhibit significant nerve conduction velocity-improving or nephropathy-ameliorating actions.

INDUSTRIAL APPLICABILITY

Because the microspheres of the present invention have a slow-release period of about two weeks to about four weeks following administration, enable a higher content of the present drug to be included, suppress an initial burst of the present drug, and enable the blood concentration of this drug to be maintained in a range suitable for manifesting the drug effects, these microspheres are useful for the prevention and/or treatment of ASO, myocardial infarction, angina, stroke, diabetes and complications thereof, renal failure, pulmonary fibrosis, pulmonary hypertension, asthma, OA, RA and osteoporosis, etc.

The invention claimed is:

1. A two to four-week long-acting microsphere, comprising ({5-[2-({[(1E)-phenyl(pyridin-3-yl)methylene]amino}oxy)ethyl]-7,8-dihydronaphthalen-1-yl}oxy)acetic acid or a salt thereof as a drug and a lactic acid/glycolic acid copolymer, wherein
   (i) an amount of lactic acid/glycolic acid copolymer per part by weight of the drug is from 3 to 10 parts by weight,
   (ii) the microsphere has an average particle size of from 20 to 50 μm, and
   (iii) the lactic acid/glycolic acid copolymer has a weight-average molecular weight of from 10,000 to 50,000 and a lactic acid/glycolic acid compositional ratio of from 75/25 to 50/50.

2. The microsphere according to claim 1, wherein the content of lactic acid/glycolic acid copolymer per part by weight of the drug is from 4 to 8 parts by weight.

3. The microsphere according to claim 1, wherein the microsphere has an average particle size of from 25 to 35 μm.

4. The microsphere according to claim 1, wherein the lactic acid/glycolic acid copolymer ratio is 50/50.

5. A method of treating arteriosclerosis obliterans, stroke, pulmonary fibrosis, pulmonary hypertension, asthma, diabetes and complications thereof, angina, myocardial infarction, heart failure, dilated cardiomyopathy, renal failure, osteoarthritis, rheumatoid arthritis or osteoporosis, comprising administering to a patient, the microsphere of claim 1.

6. A two-week long-acting microsphere, comprising ({5-[2-({[(1E)-phenyl(pyridin-3-yl)methylene]amino}oxy)ethyl]-7,8-dihydronaphthalen-1-yl}oxy)acetic acid or a salt thereof as a drug and a lactic acid/glycolic acid copolymer, wherein
   (i) an amount of lactic acid/glycolic acid copolymer per part by weight of the drug is from 4 to 8 parts by weight,
   (ii) the microsphere has an average particle size of from 25 to 35 μm, and
   (iii) the lactic acid/glycolic acid copolymer has a weight-average molecular weight of from 10,000 to 30,000 and a lactic acid/glycolic acid compositional ratio of 50/50.

7. A four-week long-acting microsphere, comprising ({5-[2-({[(1E)-phenyl(pyridin-3-yl)methylene]amino}oxy)ethyl]-7,8-dihydronaphthalen-1-yl}oxy)acetic acid or a salt thereof as a drug and a lactic acid/glycolic acid copolymer, wherein
   (i) an amount of lactic acid/glycolic acid copolymer per part by weight of the drug is from 4 to 8 parts by weight,
   (ii) the microsphere has an average particle size of from 25 to 35 μm, and
   (iii) the lactic acid/glycolic acid copolymer has a weight-average molecular weight of from 30,000 to 50,000 and a lactic acid/glycolic acid compositional ratio of 50/50.

* * * * *